US012102350B2

(12) United States Patent
Ibrahim et al.

(10) Patent No.: US 12,102,350 B2
(45) Date of Patent: Oct. 1, 2024

(54) SCOPE AND MAGNETIC INTRODUCER SYSTEMS AND METHODS

(71) Applicant: AtriCure, Inc., Mason, OH (US)

(72) Inventors: Tamer Ibrahim, Danville, CA (US); Michael J. Banchieri, Discovery Bay, CA (US); Tony Wong, Tracy, CA (US); Dwight P. Morejohn, Davis, CA (US)

(73) Assignee: AtriCure, Inc., Mason, OH (US)

( * ) Notice: Subject to any disclaimer, the term of this patent is extended or adjusted under 35 U.S.C. 154(b) by 472 days.

(21) Appl. No.: 17/316,374

(22) Filed: May 10, 2021

(65) Prior Publication Data

US 2022/0096121 A1    Mar. 31, 2022

Related U.S. Application Data

(63) Continuation of application No. 16/173,991, filed on Oct. 29, 2018, now abandoned, which is a (Continued)

(51) Int. Cl.
| | |
|---|---|
| *A61B 17/34* | (2006.01) |
| *A61B 1/00* | (2006.01) |
| *A61B 1/313* | (2006.01) |
| *A61B 17/00* | (2006.01) |
| *A61M 1/00* | (2006.01) |

(52) U.S. Cl.
CPC ...... *A61B 17/3421* (2013.01); *A61B 1/00154* (2013.01); *A61B 1/3132* (2013.01); *A61B 2017/00243* (2013.01); *A61B 17/3462* (2013.01); *A61B 2017/347* (2013.01);
(Continued)

(58) Field of Classification Search
CPC ............ A61B 17/3421; A61B 1/00154; A61B 1/3132; A61B 17/3462; A61B 2017/00243; A61B 2017/347; A61B 2217/005; A61B 2217/007; A61M 1/85
See application file for complete search history.

(56) References Cited

U.S. PATENT DOCUMENTS 6,321,106 B1 * 11/2001 Lemelson ......... A61M 25/0068
600/407
10,123,821 B2    11/2018 Ibrahim et al.
(Continued)

*Primary Examiner* — Richard G Louis
(74) *Attorney, Agent, or Firm* — Levine Bagade Han LLP

(57) ABSTRACT

Exemplary scope systems and methods involve a cannula assembly, a sheath assembly, and a tubing set. A cannula assembly, which may be a non-magnetic scope cap assembly, can include a cannula body, a proximal housing having a strap, an optical window, and a luer for suction or flushing. A cannula body may include a first lumen or scope channel for receiving a visualization device such as an endoscope or laparoscope, a distal end having suction or flushing flush apertures, and a second lumen for providing fluid communication between the apertures and the luer. Exemplary magnetic introducer systems and methods involve a cannula assembly, a sheath assembly, a tubing set. In some cases, the cannula assembly of a magnetic introducer system can be a magnetic scope cap assembly. In addition to cannula and sheath assemblies, magnetic introducer systems can include a magnetic introducer tubing assembly and a stylet assembly.

8 Claims, 18 Drawing Sheets

Related U.S. Application Data continuation of application No. 12/879,106, filed on Sep. 10, 2010, now Pat. No. 10,123,821.

(60) Provisional application No. 61/241,297, filed on Sep. 10, 2009.

(52) U.S. Cl.
CPC ... *A61B 2217/005* (2013.01); *A61B 2217/007* (2013.01); *A61M 1/85* (2021.05)

(56) References Cited

U.S. PATENT DOCUMENTS

| | | | |
|---|---|---|---|
| 2004/0102804 A1 | 5/2004 | Chin | |
| 2005/0182299 A1* | 8/2005 | D'Amelio | G02B 23/2423 600/172 |
| 2006/0015131 A1* | 1/2006 | Kierce | A61B 34/73 606/191 |
| 2006/0189972 A1* | 8/2006 | Grossman | A61B 18/1477 606/41 |
| 2006/0252993 A1* | 11/2006 | Freed | A61B 1/0052 604/95.04 |
| 2006/0253077 A1 | 11/2006 | Smith | |
| 2007/0016276 A1* | 1/2007 | Heil, Jr. | A61N 1/3629 607/119 |
| 2007/0249899 A1* | 10/2007 | Seifert | A61B 1/0004 600/176 |
| 2009/0163768 A1 | 6/2009 | Ibrahim et al. | |
| 2019/0125400 A1 | 5/2019 | Ibrahim et al. | |
| 2020/0100789 A1 | 4/2020 | Bertolero et al. | |

* cited by examiner

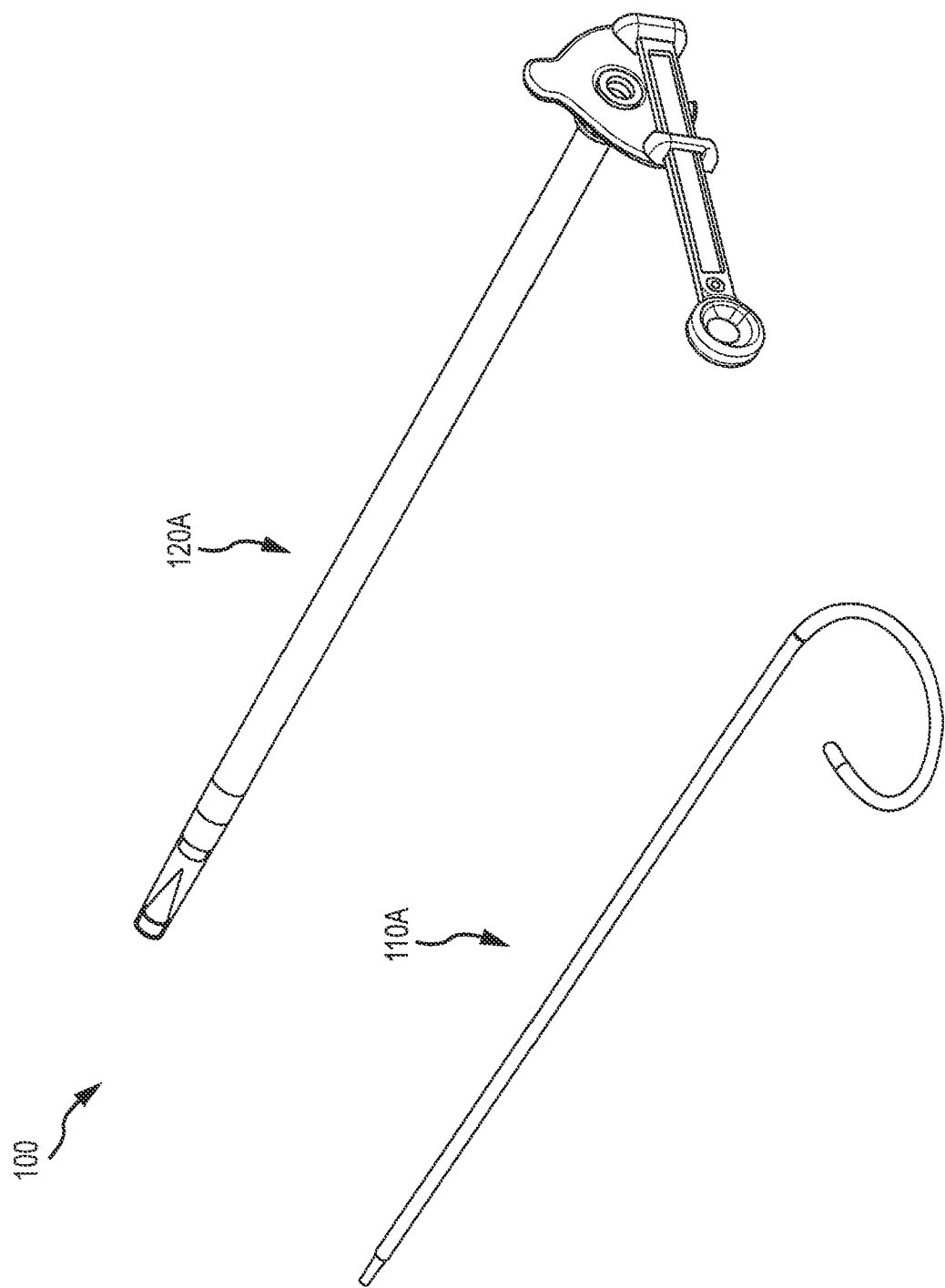

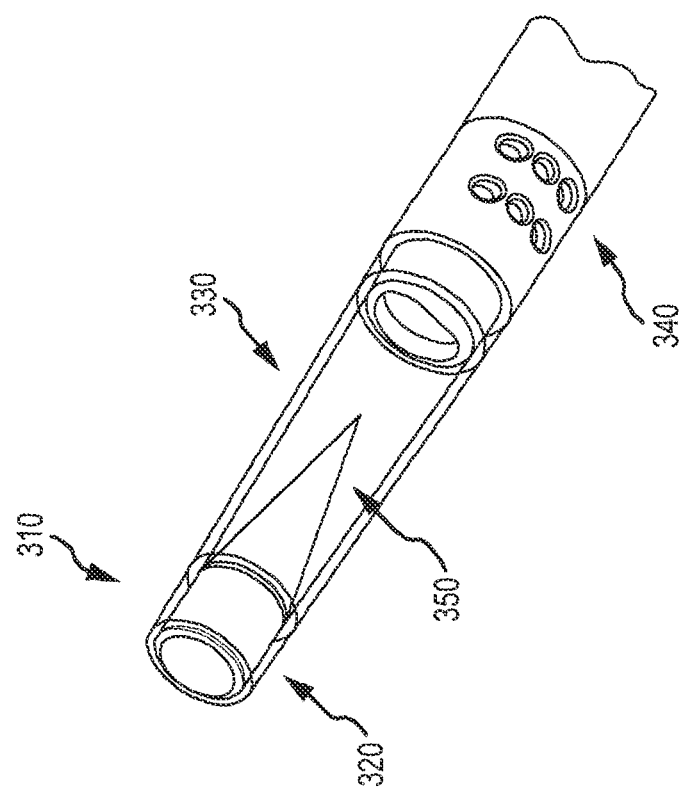
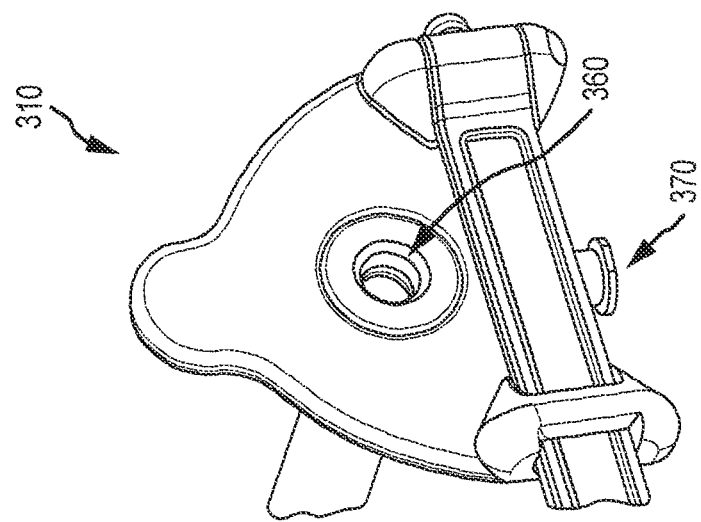
FIG. 3

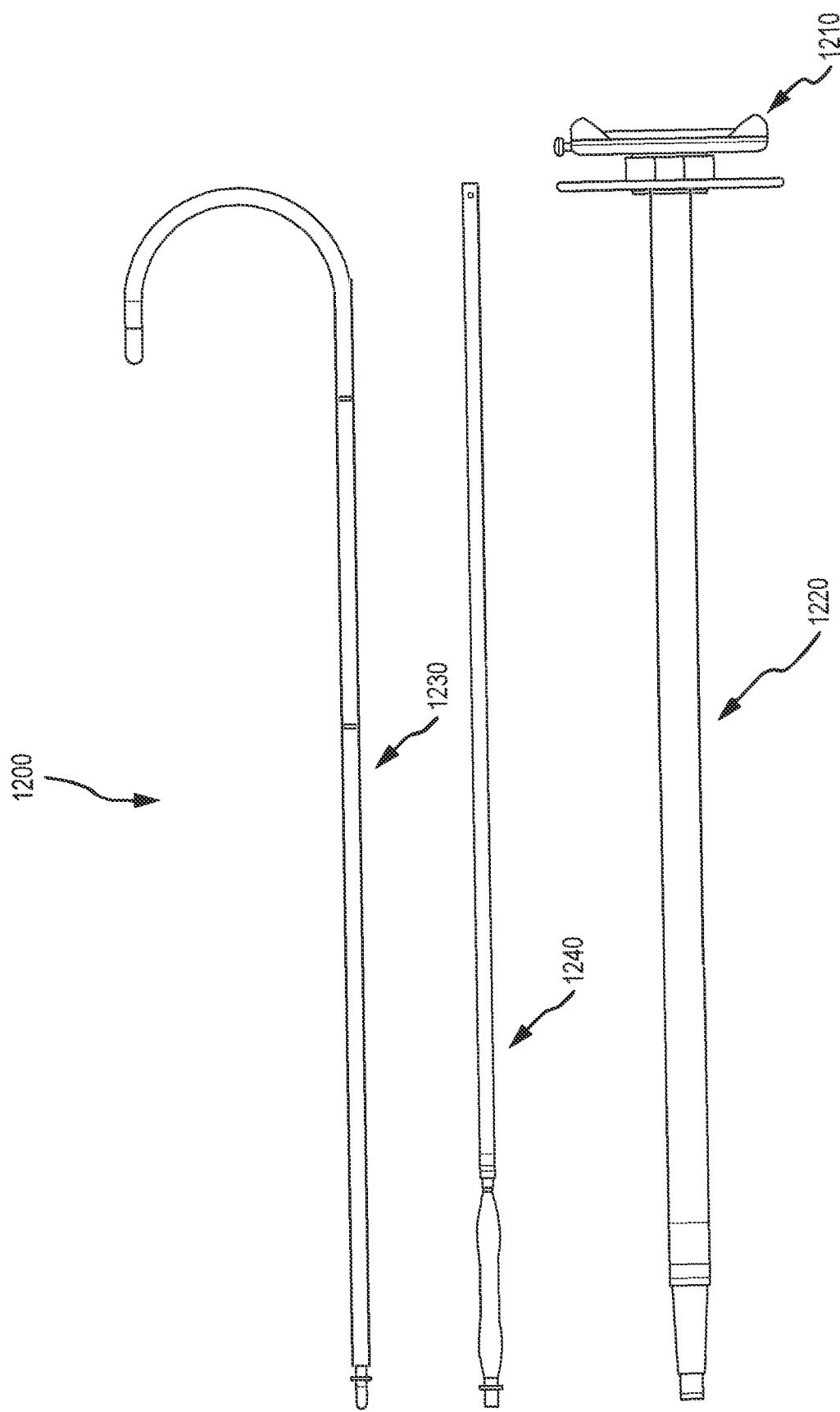

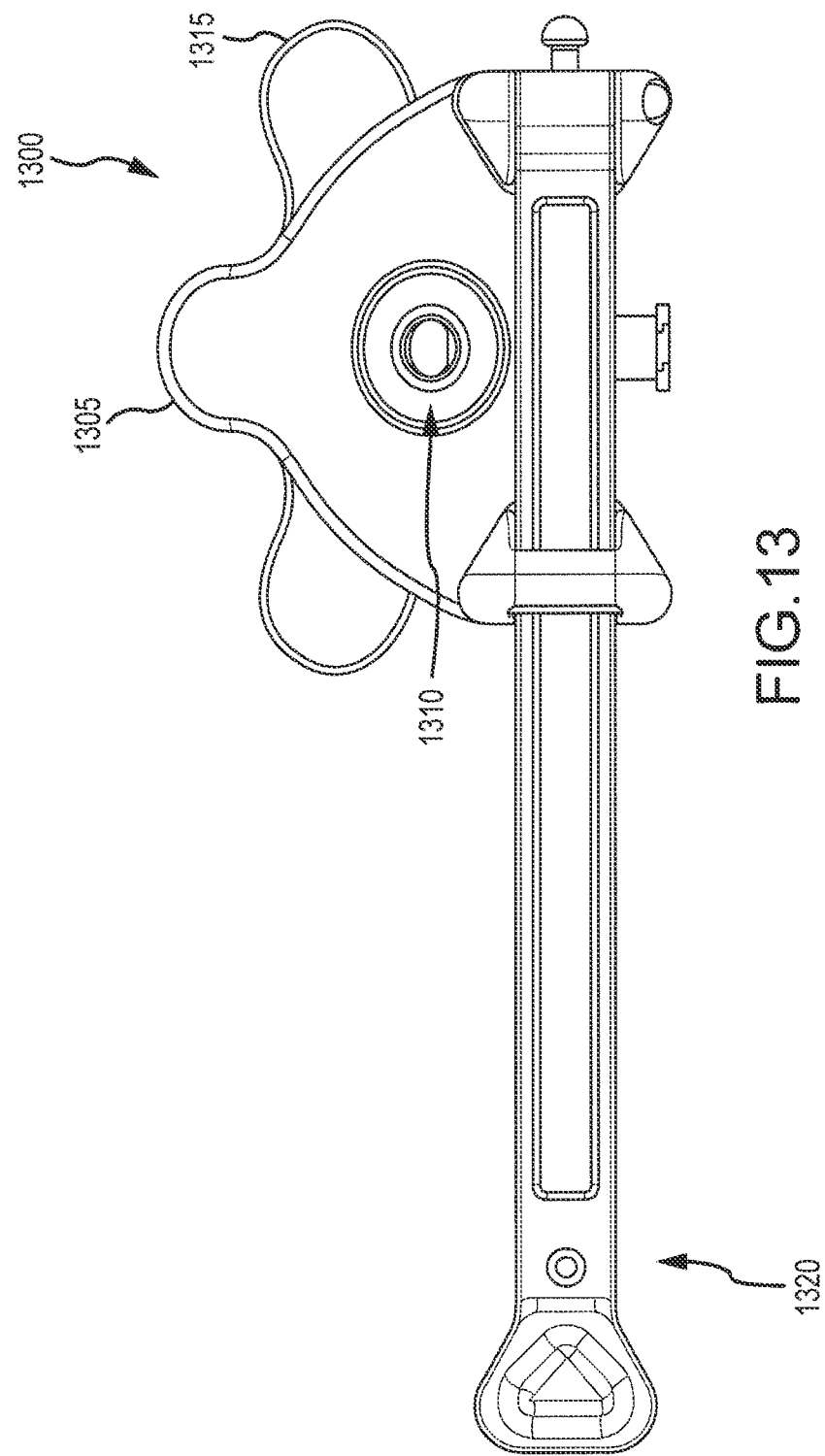

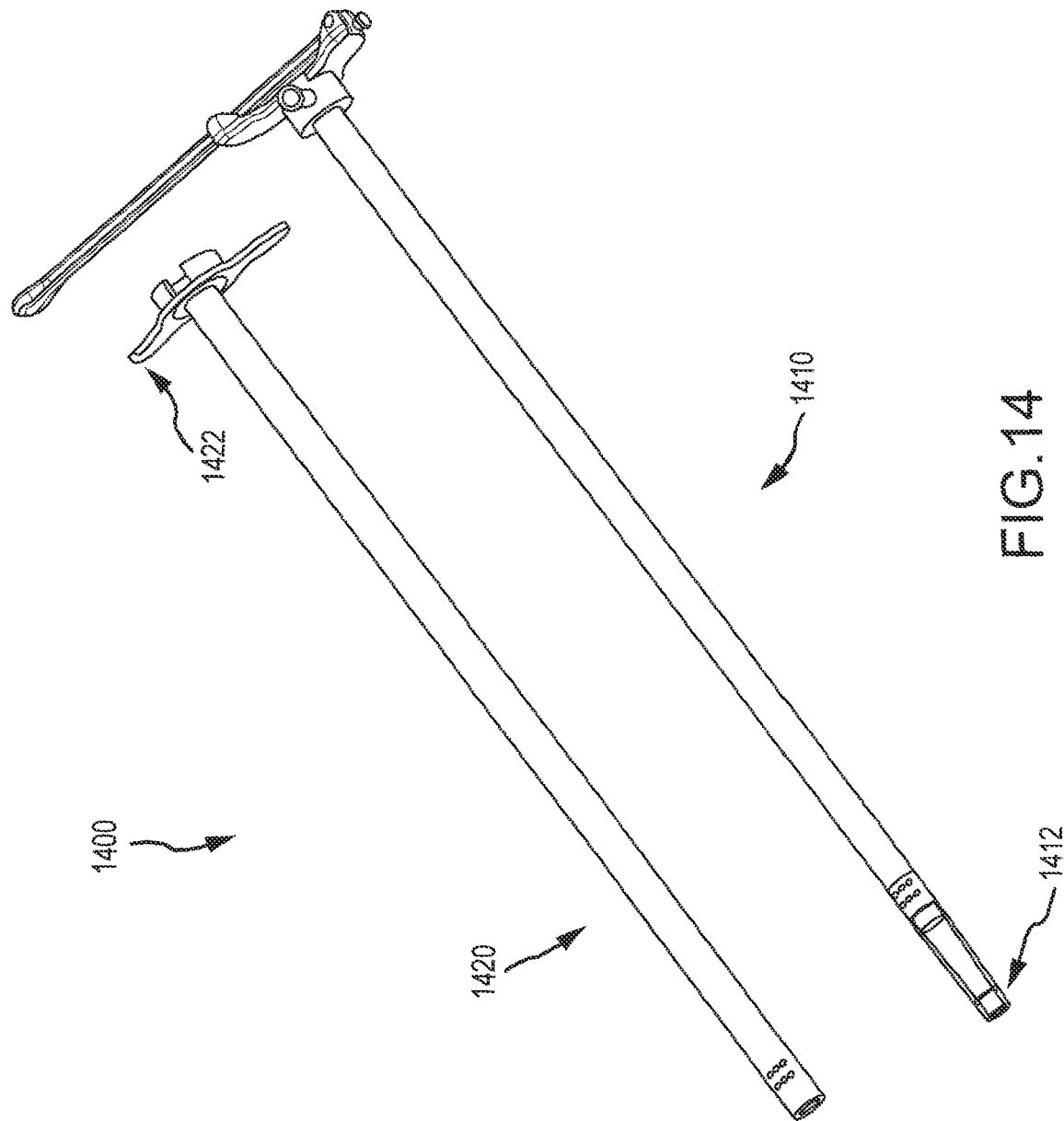

SCOPE AND MAGNETIC INTRODUCER SYSTEMS AND METHODS

CROSS-REFERENCE TO RELATED APPLICATIONS

This application is a continuation of Ser. No. 16/173,991 filed Oct. 29, 2018 which is a continuation U.S. patent application Ser. No. 12/879,106 filed Sep. 10, 2010 (now U.S. Pat. No. 10,123,821), which claims benefit of U.S. Provisional Patent Application No. 61/241,297 filed Sep. 10, 2009, the contents of which are incorporated herein by reference in their entirety. This application is also related to U.S. Patent Application No. 60/939,201 filed May 21, 2007, U.S. Patent Application No. 61/015,472 filed Dec. 20, 2007, U.S. patent application Ser. No. 12/124,743 file May 21, 2008, U.S. patent application Ser. No. 12/124,766 filed May 21, 2008, U.S. patent application Ser. No. 12/339,331 filed Dec. 19, 2008, and U.S. Patent Application No. 61/179,564 filed May 19, 2009. The entireties of each of these filings is incorporated herein by reference for all purposes.

BACKGROUND OF THE INVENTION

Embodiments of the present invention relate generally to medical devices and methods, and in particular to positioning systems and methods for cardiac ablation procedures.

Medical treatment and surgical methods typically involve a surgeon or operator placing a treatment device at a desired location within a patient. For example, a surgeon can position a cardiac ablation device in the vicinity of a patient's heart, and apply an ablative energy to the epicardial tissue to treat atrial fibrillation and other arrhythmias. Often, treatment devices are difficult to accurately position at an effective location within the patient. Relatedly, surgeons may find it difficult to adequately secure a treatment device at a desired location in the patient. Another shortcoming of currently available surgical techniques is the difficulty of gaining optimal visualization of a surgical or treatment site on the heart or of structures in and around the surgical site. In other words, gaining sufficient visualization to allow the surgeon to accurately manipulate, ablate, or otherwise operate at a specific location within the patient's body is sometimes challenging using current methods and devices. Oftentimes, visualization devices and surgical instruments collide or simply overcrowd a surgical site, reducing a surgeon's room to work in and visualize the surgical site.

Therefore, there continues to be a need for devices, systems, and methods for positioning a treatment device at a desired location in the patient. In some embodiments, devices and methods would provide enhanced techniques for viewing within the body of the patient to facilitate placement of the treatment devices, without crowding the surgical site. Optionally, embodiments may involve improved techniques for attaching or securing a treatment device at a location within a patient. Further, it would be desirable for such methods and devices to be minimally invasive. At least some of these objectives will be met by embodiments of the present invention.

BRIEF SUMMARY OF THE INVENTION

Embodiments of the present invention provide techniques that are well suited for placing a treatment device at a location within a patient. Such techniques involve the use of introducer devices having coupling mechanisms, and optionally integrated visualization mechanisms, whereby an operator can efficiently and effectively manipulate the introducer devices within the patient's body so as to position a treatment device at a desired location. Advantageously, such techniques can be performed in a minimally invasive procedure without crowding the surgical site.

In one aspect, embodiments of the present invention encompass devices and methods for placing a treatment device at a location within a patient. A placement device can include a cannula assembly having a first lumen and a second lumen, wherein the first lumen extends into a distal portion of the cannula assembly, wherein the first lumen is adapted for receiving, and providing an optical window for, an endoscope, laparoscope, or other imaging device, and wherein the second lumen includes an aperture near a distal section of the cannula assembly. The placement device can also include a connection at the proximal end of the cannula assembly to provide fluid communication for flushing or suction at the second lumen aperture, and an attachment mechanism for removably attaching the cannula assembly to a treatment device. In some cases, the attachment mechanism operates to connect the treatment device to the distal end of the cannula assembly. In some cases, the attachment mechanism uses magnetic force to attach the treatment device to the cannula assembly. Optionally, a seal is provided to inhibit fluid ingress into the first lumen after the imaging device is inserted into the cannula assembly. According to some embodiments, a magnet is located within the distal section of the cannula assembly. A retention mechanism can maintain the imaging device at a stable location within the first lumen. A retaining means can include a strap. In some cases, an attachment mechanism operates to connect to an ablation device. In some cases, an attachment mechanism operates to connect to pacing electrodes. Optionally, the distal end of the cannula assembly can carry pacing electrodes. Relatedly, the distal end of the cannula assembly can carry ablation elements. In some cases, the distal end of the cannula assembly can carry ablation elements. The ablation elements may heat tissue using radiofrequency energy, microwave energy, or ultrasonic energy. In some cases, the ablation elements freeze tissue to achieve ablation.

In another aspect, embodiments of the present invention encompass magnetic introducer systems and methods. Exemplary magnetic introducer systems include a cannula assembly, a sheath assembly, a tubing set, a magnetic introducer tubing assembly, and a stylet assembly. In some cases, the cannula assembly includes a magnetic scope cap assembly. In some cases, the magnetic introducer tubing assembly includes a pre-formed shape or bend. Optionally, the sheath assembly can be configured to receive a distal end of the magnetic introducer tubing.

For a fuller understanding of the nature and advantages of the present invention, reference should be had to the ensuing detailed description taken in conjunction with the accompanying drawings.

BRIEF DESCRIPTION OF THE SEVERAL VIEWS OF THE DRAWINGS

FIGS. 1A and 1B illustrate aspects of scope and magnetic introducer systems and methods according to embodiments of the present invention.

FIG. 3 depicts aspects of scope and magnetic introducer systems and methods according to embodiments of the present invention.

FIG. 12 illustrates aspects of scope and magnetic introducer systems and methods according to embodiments of the present invention.

FIG. 13 shows aspects of scope and magnetic introducer systems and methods according to embodiments of the present invention.

FIG. 14 depicts aspects of scope and magnetic introducer systems and methods according to embodiments of the present invention.

DETAILED DESCRIPTION OF THE INVENTION

Figure 1B:
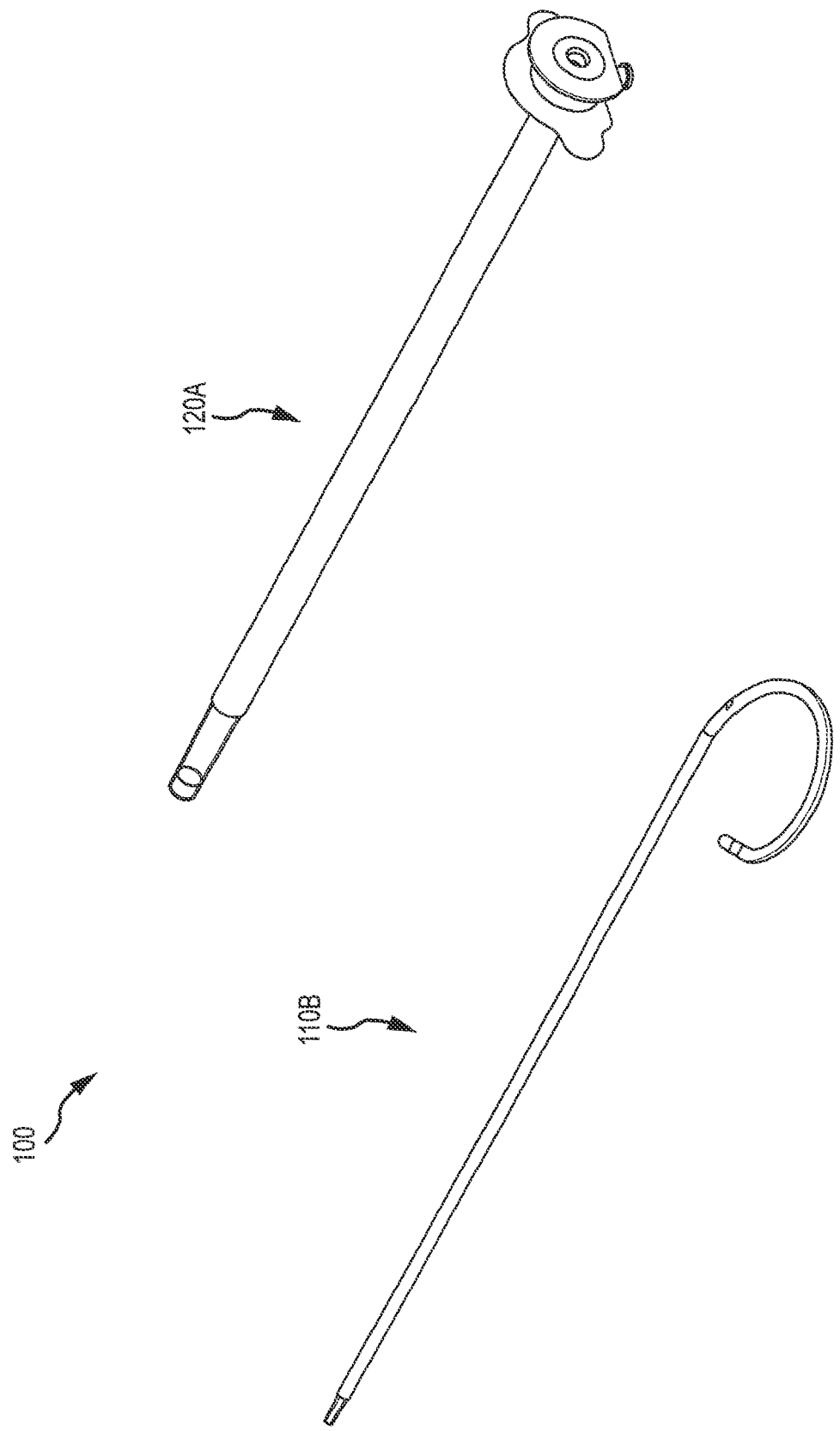

Embodiments of the present invention encompass scope and magnetic introducer systems and methods for their use in surgical procedures.

Scope Systems and Methods

Exemplary scope systems include a cannula assembly, a sheath assembly, and a tubing set.

A cannula assembly, which in some cases may be a non-magnetic scope cap assembly, may include a cannula body, a proximal housing having a strap, an optical window, and a luer for suction or flushing. A cannula body may include a first lumen or scope channel for receiving a visualization device such as an endoscope or laparoscope, a distal end having suction or flushing flush apertures, and a second lumen for providing fluid communication between the apertures and the luer. The cannula body can be sealed to prevent or inhibit liquid and tissue from contacting the visualization device or scope. The proximal housing may include a scope port for a visualization device such as an endoscope. The optical window may include a non-magnetic distal cap. The suction or flushing luer may include a service port on a proximal end having female luer connector that can accommodate standard or vacuum source or that can be used for flushing purposes. In some cases, the luer can be configured to interface with a standard luer syringe and standard wall vacuum source, for example when flushing or suction features are being used.

A sheath assembly may include a sheath body and a flange. In some cases, the sheath body may be a removable sheath. The sheath body can be configured to slide over the cannula. The distal end of the sheath may terminate just proximal to the viewing window of the cannula assembly so as to remain out of view or alternatively may extend beyond the window. The sheath tip may be blunted and comprise an alternate soft, flexible material as compared to the material of the body of the sheath. The flange may be configured to be easily removed from the sheath body. In some cases, the flange can be easily snapped on or off.

In use, the cannula, with the endoscope or visualization device, and the sheath are positioned in the patient. The cannula and visualization device can be removed, leaving the sheath positioned within the patient. Subsequently, medical treatment devices can be inserted or introduced within the sheath.

Magnetic Introducer Systems and Methods

Exemplary magnetic introducer systems include a cannula assembly, a sheath assembly, a tubing set, as described above in relation to the scope systems. In some cases, the cannula assembly of a magnetic introducer system can be a magnetic scope cap assembly. In addition to cannula and sheath assemblies, magnetic introducer systems can include a magnetic introducer tubing assembly and a stylet assembly.

A magnetic introducer tubing assembly can have a preformed shape or bend, and can be used in conjunction with an obturator or stylet. According to some embodiments, after a cannula assembly is removed from a sheath assembly, a distal end of a magnetic introducer tubing is inserted into the sheath assembly. The cannula assembly can be used through a different port or access site. Exemplary techniques can also involve using a distal visualization tip of the cannula assembly to visualize and attach with the magnetic introducer tubing or other instrument. Methods can also include withdrawing the magnetic cannula, thus pulling the introducer tubing along. It is possible to attach treatment devices with the introducer tubing which can then be advanced into the patient. Certain surgical approaches may also involve the use of a cannula assembly to confirm the placement of the treatment device.

A stylet can be configured to interface with the magnetic introducer tubing assembly. In some cases, the stylet is configured as an obturator.

Tubing Set

As noted above, scope systems as well as magnetic introducer systems may include a tubing set. According to some embodiments, a tubing set includes a first tubing assembly that provides fluid communication between a vacuum source and a canister, a second tubing assembly that provides fluid communication between a canister and a sterile field, a third tubing assembly that is configured to couple with a stopcock, and a fourth tubing assembly that provides fluid communication between a stopcock and a treatment device. In some cases, the fourth tubing assembly may include a stopcock.

In some cases, the first tubing assembly may include a suction tubing having a length of about three feet, an inner diameter (ID) of about 0.25 inches, and an outer diameter (OD) of about 0.375 inches.

In some cases, the second tubing assembly may include a suction tubing having a length of about twelve feet and an inner diameter (ID) of about 0.25 inches.

In some cases, the third tubing assembly may include a suction tubing having a length of about three feet, an inner diameter (ID) of about 0.125 inches, and an outer diameter (OD) of about 0.25 inches. The third tubing assembly may provide a connection between the second tubing assembly and a stopcock.

In some cases, the first tubing assembly may include a suction tubing having a length of about one foot and an inner diameter (ID) of about 0.125 inches. The fourth tubing assembly can provide fluid communication between a stopcock and a treatment device. In some cases, the fourth tubing assembly includes or is attached with a stopcock.

Exemplary Embodiments (Section 1)

Scope systems are well suited for use in minimally invasive surgery and provide access for delivery and placement of surgical instruments such as suction stabilizers or pacing probes. Scope systems can be used for treating patients that may benefit from blunt dissection of tissue including structures in the thoracic space.

Magnetic introducer systems are well suited for use in minimally invasive surgery and provide access for delivery and placement of surgical instruments such as ablation probes, suction stabilizers, or pacing probes. Magnetic introducer systems can be used for treating patients that may benefit from blunt dissection of tissue including structures in the thoracic space.

Scope systems and magnetic introducer systems can be configured to interface with a standard luer syringe and standard wall vacuum source when suction or flush features are being used. Introducer system can be compatible with suction stabilizers in terms of introducer routing and retrieval. Scope systems and magnetic introducer systems can be used for general visualization and dissection with any of a variety of treatment devices. Scope systems and magnetic introducer systems may be packaged sterile (EtO), for single use. Individual components of scope systems and magnetic introducer systems can be snap fitted into a tray and double pouched in Tyvek/poly peel pouches.

Scope and magnetic introducer systems can be used in any thoracoscopic or laparoscopic procedure, and particularly in those for which visualization in tight spaces is needed or desired. Scope and magnetic introducer systems can also be used in procedures which benefit from the retrieval of introducers or instruments that could be simplified by the use of magnets. Exemplary techniques may involve the use of RF ablation procedures using thoracotomy and port access approaches. For example, a thoracotomy procedure may involve creating an incision having a length of about 1-15 cm, at or near the second, third, or fourth intercostal space, located as medial as the nipple, and optionally more lateral. Scope and magnetic introducer systems may benefit from right sided access when used with suction stabilizers or pacing probes. If the surgeon so desires, a device can be inserted into a left sided access location for additional visualization or alternate routing techniques. Left sided access may be desired if a surgeon wishes to manage the left atrial appendage. Other uses of a visualization and magnetic introducer system can involve a snaring system to mobilize the aorta for proximal anastamosis during minimally invasive valve surgery, delivery of a left atrial appendage closure clip or snare, or delivery of an aortic closure clip or snare.

Surgical techniques can involve accessing sites within the patient via selected port locations. According to some embodiments, three port locations are used, including a lateral port in each of the second/third and fifth/sixth intercostals spaces, and a more medial port in the third/fourth intercostals space. In some cases, three valved ports may be used, the two lateral ports may be a minimum of 11 mm and the medial port can be as small as 5 mm if a secondary laparoscope is used for bird's eye visualization, or 11 mm to allow for use of a cannula assembly according to embodiments of the present invention.

Scope and magnetic introducer systems may in some cases only require right sided access when used with suction stabilizers or pacing probes, and if the surgeon desires, components of the system can be inserted into left sided ports for additional visualization or alternate routing techniques. The two lateral ports can be used for the entry and exit of the a magnetic introducer system and ablation device, for example. The medial port can be used for a general or bird's eye visualization of the surgical site, additional tissue dissection tools, or for inserting a scope cannula to confirm device placement.

Scope and magnetic introducer techniques can involve dissection for device access to the heart. For example, the pericardium can be opened 1-2 cm anterior to the phrenic nerve from the superior vena cava (SVC) down toward the diaphragm. Blunt dissection between the inferior pulmonary vein and the inferior vena cava (IVC) under the left atrium can be used to enter the oblique sinus. Blunt dissection under the SVC can be used to enter the transverse sinus. When using left-sided ports or thoracotomy, the pericardium can be entered posterior to the left phrenic nerve and the incision extended to enable unencumbered access to the base of the left atrial appendage. Throughout the surgical procedure, care is typically taken to avoid cutting, stretching, or grasping the phrenic nerves.

Exemplary surgical methods can involve inserting a 5 to 5.5 mm endoscope into the opening on the proximal end of the cannula assembly and installing the sheath onto the cannula. A camera and light guide cable can be connected to the endoscope. The female luer can be connected to standard wall suction and/or flush tubing. The scope system can be introduced through a superior, lateral port or thoracotomy, and navigated into the transverse sinus and across until the left side of the pericardium is visualized. The cannula can be detached from the sheath and withdrawn using reasonable force while holding to sheath in place. In order to maintain insufflation pressures it may be desirable for the sheath to include an expandable seal at its proximal end to allow for the accumulation of pressure inside the chest as instruments are introduced through the seal. The seal may be configured to have an inner diameter (ID) appropriately sized such that accumulation of the pressure remains possible if no instrument is inserted into the seal, for example <2 mm in diameter. Such a seal can be integrated into the sheath or alternatively can be a separate snap-in component that is inserted once the cannula is removed. The distal end of the magnetic introducer tubing can be inserted into the sheath and advanced until a second ring mark on the magnetic introducer tubing is aligned with the entrance of the sheath. Once separated, the cannula and sheath may be advanced along side one another. The sheath may be clear or transparent such that a scope may be introduced directly into it and visualization provided. Depth markings may be placed along the length of the sheath for aiding introduction and making it more easily visible by the scope. Alternatively, the sheath may be translucent. The cannula can be inserted (with sheath detached) into the inferior, lateral port or thoracotomy and navigated into the oblique sinus.

The tip of the magnetic introducer tubing can be visualized and retrieved with either the magnetic cannula or another instrument. The magnetic cannula or instrument can be withdrawn while advancing the introducer until the proximal end of the introducer nears the entrance to the port.

When a magnetic introducer system is used in conjunction with a suction stabilizer, it may be beneficial to attach a distal tubing of the suction stabilizer to the proximal end of the magnetic introducer tubing, for example to ensure that the stripe on both tubes is aligned. Using reasonable force, it is possible to continue pulling the magnetic introducer tubing out of the port/incision, while advancing the suction stabilizer. When a distal tubing of the suction stabilizer is out of the chest wall, it is possible to disconnect the magnetic introducer tubing from the device. After the suction stabilizer or other device has been placed, the cannula can be reinserted into any of the ports to confirm placement of the device. If desired, a stylet can be used during the introduction of a magnetic introducer tubing into a luer of a sheath.

Scope and magnetic introducer systems may in some cases be compatible with 0 degree, 5-5.5 mm laparoscopes with a minimum working length of 30 cm. Various other scopes are suitable. The size of the cannula can be adjusted to accommodate scopes of various lengths and diameters. Additional various angled scopes can be used such as a 30 or 45 degree scope providing a more lateral view of adjacent tissues or even 120-180 degree scopes that integrate mirror technology to provide a hindsight view to the system. Exemplary magnetic introducer systems can be configured to fit through a 10 mm port. According to some techniques, clear visualization can be provided within the chest wall. Cannulas can provide a port for suction/flushing. A distal window of a cannula can be sealed to prevent liquid and tissue from contacting the scope. In some cases, a distal end of a magnetic introducer tubing can be pre-formed into a 270.degree., 1.5" bend radius with 1.33" helical pitch. Magnetic introducer tubing can be configured to return to an original bend radius when the obturator is withdrawn from introducer tube or when the introducer is fully projected out of the sheath using markings as described above. Introducer tubing may have a linear marking along its lengths to properly align components during connection. An introduction system may include a means for easily retrieving a distal tip. In some cases, a magnetic introducer system can be designed for single use. Optionally, introducer tubing can have indication marks to determine the location of a magnetic tip relative to the tip of the sheath.

Scope and introducer systems can be packaged with tube sets which include tubes of various configurations. An exemplary tube set includes a 3' length of ¼" ID for connection from wall source to canister, a 12' length of ¼" ID for connection from canister to sterile field, a 3' length of ⅛" ID to connect from 12' length to stopcock, and a 1' length of ⅛" ID to connect from stopcock to device. Scope and introducer systems can be packaged in a thermoformed tray, double pouched, and inserted into a chipboard unit box.

Exemplary Embodiments (Section 2)

As depicted in FIGS. 1A and 1B, magnetic introducer systems can include an introducer assembly and a scope cap assembly. As shown here, magnetic introducer system 100 includes an introducer assembly such as a magnetic introducer 110A or an introducer 110B. Magnetic introducer system 100 also includes a scope cap assembly such as a magnetic scope cannula 120B or a scope cap 120B.

Table 1 depicts various attributes of introducer devices according to embodiments of the present invention.

TABLE 1

| Attribute | Introducer Design A | Introducer Design B |
|---|---|---|
| Tubing material | Braided PUR | Unbraided Pebax |
| Tubing dimensions | OD: .198, ID: .155 | OD: .250, ID: .125 |
| Tip retrieval design | Surgical tape | Magnet |
| Tip diameter | .300" | .233" |
| Bend radius | 1" | 1.50" |
| Helical pitch none | none | 1.33" |
| Proximal connection | Barbed connector | Barbed connector |
| Orientation indicator | Axial stripe | Axial Stripe |

According to some embodiments, it is desirable to use a smaller diameter tubing for an introducer. Relatedly, it may be desirable to provide adequate magnet strength with, for example, a 0.250 OD magnet. In some cases, a smaller diameter tubing (e.g. 0.187") may be used, and the distal tip of the introducer (magnet) can be larger in diameter than the tubing, for a particular magnetic tip introducer set. Alternatively, it is possible to make the OD of the tubing the same diameter as the OD of the magnet. The introducer tubing can still be smaller than the ablation device which follows it. Therefore, having a slightly larger introducer tubing may benefit introduction by providing some dilation of the transverse and oblique sinus spaces.

To adjust the perception of the distal end of the introducer, a taper can be added (0.233" dia. at the tip to 0.250" dia. at the proximal end of the exposed magnet (0.500" from the distal tip). The taper typically does not have a significant impact on the magnetic coupling strength between the scope cap and the introducer. The Pebax material used on Design B may be silicone coated to increase lubricity to aid in insertion. The stylet can still be included in the system, although it may not be necessary if the scope cap sheath is used as described below.

Figure 2:
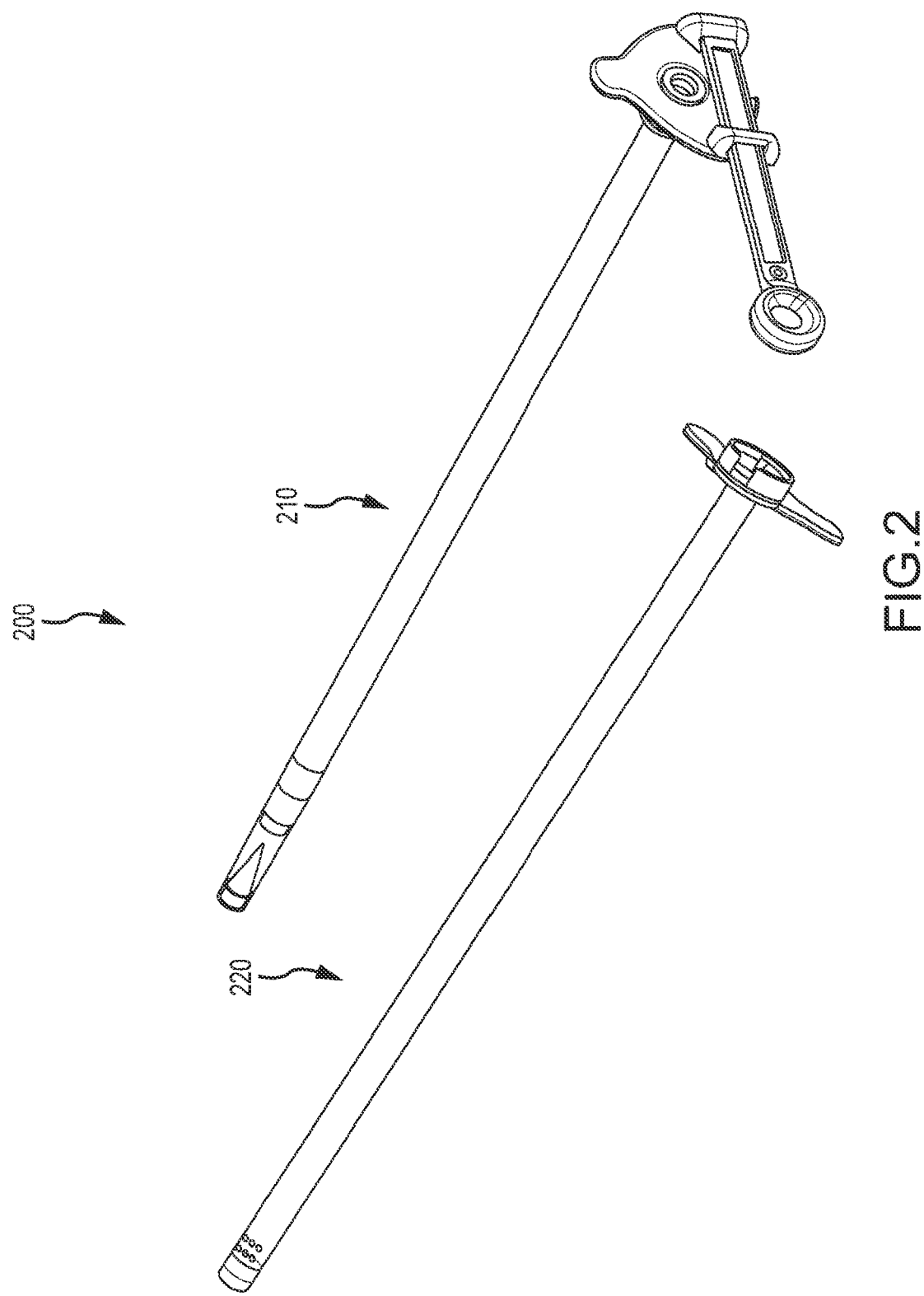
FIG. 2 shows aspects of scope and magnetic introducer systems and methods according to embodiments of the present invention.

As depicted in FIG. 2, a scope cap assembly 200 can include two main components. The first component can be embodied as a scope cap such as a magnetic scope cannula 210 that houses the magnet, distal window, scope channel, and suction/flushing port. The second component can be embodied as a sheath 220, which slides over the scope cap or magnetic scope cannula 210. In use, the sheath can be assembled over the scope cap. It is thus possible to dissect across the transverse sinus under endoscopic visualization, and then remove the scope cap 210 while keeping the sheath 220 in place. The sheath 220 then provides a channel to advance an introducer assembly, such as magnetic introducer 110A depicted in FIG. 1A or introducer 110E depicted in FIG. 1B, across the transverse sinus.

FIG. 3 illustrates additional aspects of treatment systems according to embodiments of the present invention. As shown here, a cannula or scope cap assembly can include a scope cap 310 having a magnet 320, a distal window 330, and one or more suction/flushing apertures or ports 340 disposed at a distal section of the scope cap. Scope cap 310 may also include a cone 350. Further, scope cap 310 may include a scope channel 360 and a suction/flushing port 370 disposed at a proximal end of the scope cap. Suction/flushing apertures may be in fluid communication with suction/flushing port.

According to some embodiments, a scope cap can be configured to fit in a minimum 11 mm port. A scope cap can provide a channel for suction/flushing. A scope cap may also be configured to work with 5 mm laparoscopes, and accommodate up to a 5.5 mm laparoscope. Scope caps may be compatible with scopes having a minimum working length of 30 cm. In some cases, a scope cap may have a working length of 28.4 cm (from port to tip of scope) and 31.7 cm (from port to tip of magnet).

In some instances, there may be a relationship between working length maximization and scope compatibility. For example, a 5 mm laparoscope can range in working length from 28 to 33 cm. In order to accommodate a short working length scope, it may be desirable to adjust or reduce the working length of the scope cap to allow the scope to fit properly. Conversely, in order to accommodate a long working length scope, it may be desirable to adjust or increase the working length of the scope cap to allow the scope to fit properly. According to some embodiments, a treatment system can accommodate a minimum scope working length of about 30 mm. Such configurations may present a compromise between scope cap working length and scope compatibility. In some cases, the working length can be added by increasing the length of the window. Variations in window length may be associated with variations in the length or distance between the magnet and the tip of the scope. In some cases, such variations can affect maneuverability or visualization of the magnet.

Exemplary scope caps may be configured to accommodate laparoscopes ranging from 5 to 5.5 mm in actual diameter. In some cases, other scope sizes may be employed. Scope caps may also be configured to accommodate suction/flushing capabilities. According to some embodiments, a small port size is used to make a procedure less invasive. Embodiments may also involve using a scope with a scope cap having a suction channel, and fitting the device through a port (e.g. 11 mm), such that the device includes a sufficiently sized magnet for performance.

Figure 4:
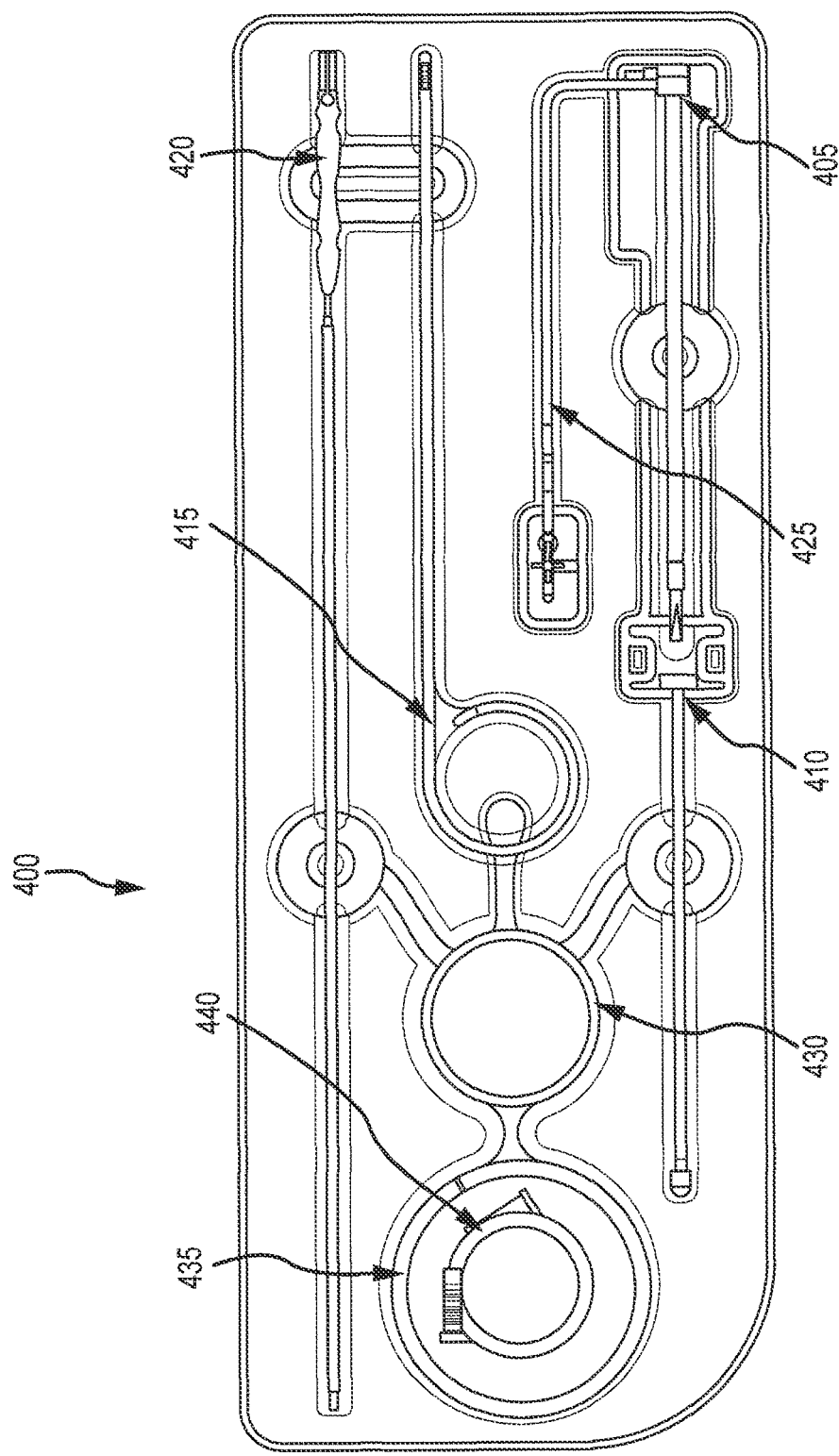
FIG. 4 shows aspects of scope and magnetic introducer systems and methods according to embodiments of the present invention.

Aspects of an exemplary treatment or introducer system are illustrated in FIG. 4. As shown here, a magnetic introducer system 400 may include a magnetic scope cap 405 with sheath 410, a Magnetic Introducer Tubing 415, a Stylet 420, a 1 foot length of ¼" OD suction tubing with attached stopcock 425, a 3 foot length of ¼" OD suction tubing 430, a 12 foot length of ⅜" OD suction tubing 435, and a 3 foot length of ⅜" OD suction tubing 440 (canister to wall suction connection). The system can be packaged in a thermoformed tray and double pouched.

According to some embodiments, a scope system may include a non-magnetic scope cap with sheath, a 1 foot length of ¼" OD suction tubing with attached stopcock, a 3 foot length of ¼" OD suction tubing, a 12 foot length of ⅜" OD suction tubing, and a 3 foot length of ⅜" OD suction tubing (canister to wall suction connection). The system can be packaged in a thermoformed tray and double pouched.

Exemplary Embodiments (Section 3)

Figure 5:
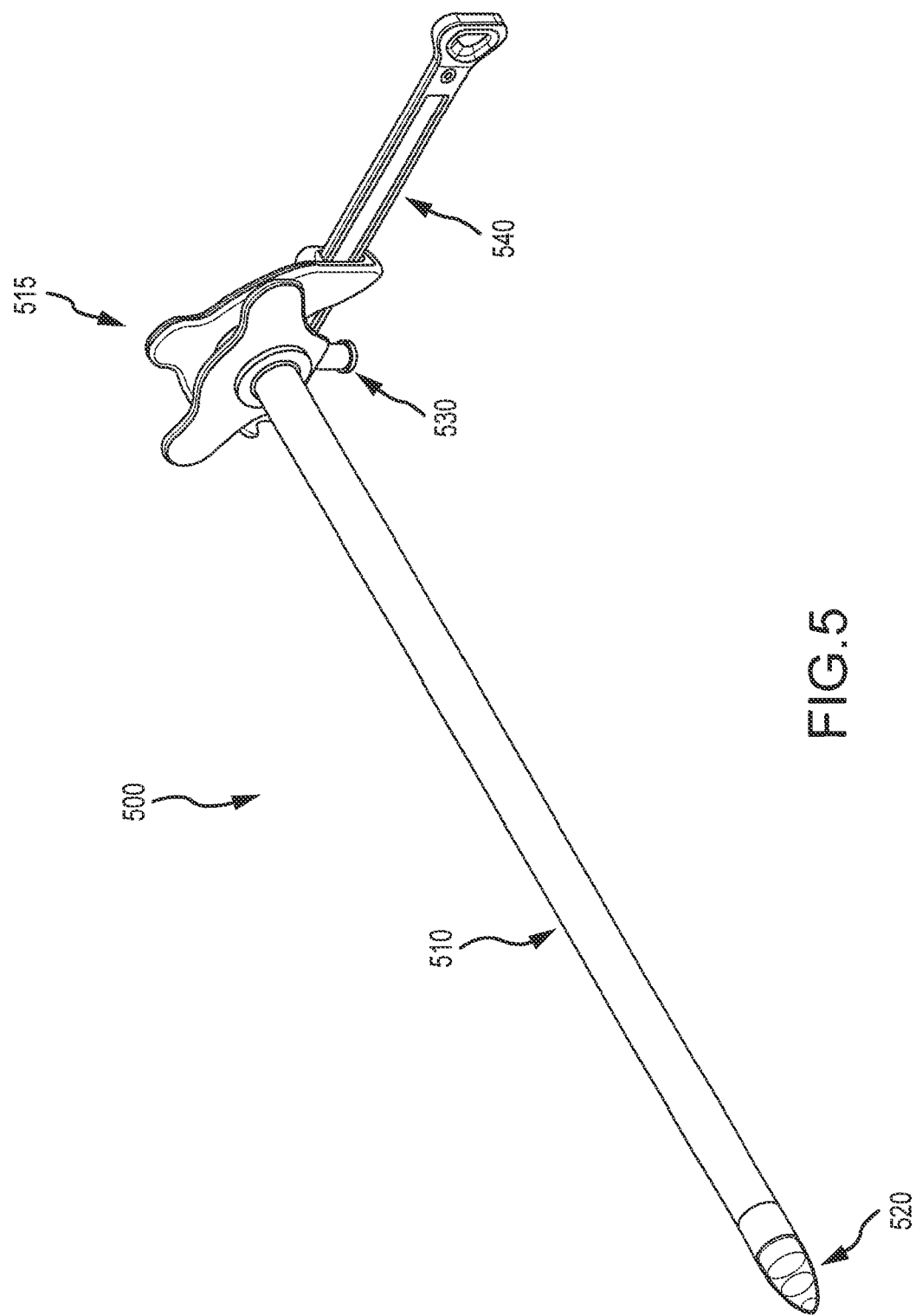
FIG. 5 depicts aspects of scope and magnetic introducer systems and methods according to embodiments of the present invention.
Figure 6:
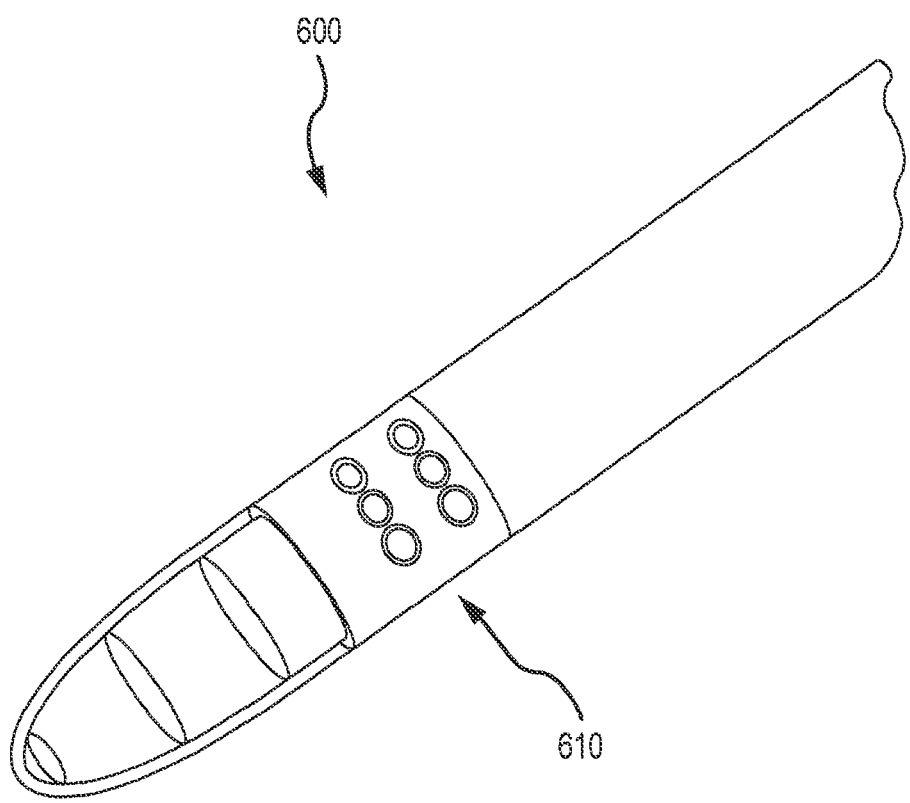
FIG. 6 illustrates aspects of scope and magnetic introducer systems and methods according to embodiments of the present invention.
Figure 7:
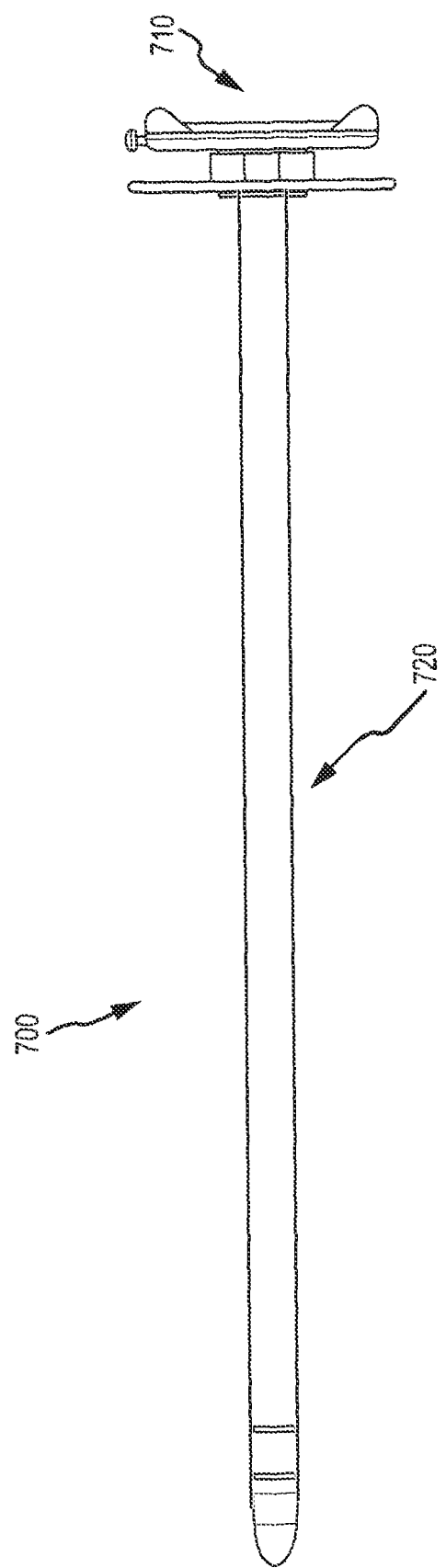
FIG. 7 shows aspects of scope and magnetic introducer systems and methods according to embodiments of the present invention.

Scope systems may be configured for use with introducer systems or other treatment devices. For example, scope systems may be configured for use with a multiple-electrode, temperature-controlled RF ablation technology device. Such devices may employ precisely controlled RF energy to create reproducible, uniform transmural lesions during cardiac surgery, such as endocardial or epicardial ablations. In some cases, a scope system may be used as a stand-alone device. Scope systems can be configured to accommodate endoscopes of various sizes. Scope systems may include features such as an optical window, a proximal housing with a strap and luer for suction or flushing, an easy snap on/off flange and removable sheath. The service port on the proximal end of the product may have a female luer connector that can accommodate a standard OR vacuum source or can be used for insufflation or flushing/irrigation purposes, as depicted in FIG. 5. As shown here, treatment system 500 includes a removable sheath 510, and a cannula or scope cap assembly 515 having a non-magnetic distal cap 520, a suction/flushing port 530, and a scope strap 540. Built-in suction/flush apertures at the distal end of the system are also depicted at FIG. 6. As shown here, treatment system 600 includes one or more suction/flushing apertures 610. An exemplary scope system 700 is also shown in FIG. 7, including a cannula or scope 710 with an assembled sheath 720.

Scope and introducer systems may be indicated for minimally invasive surgery, and can allow access and visibility for delivery/placement of surgical instruments such as ablation devices. In some cases, scope and introducer systems may be indicated for patients who may benefit from blunt dissection of tissue including structures in the thoracic space.

Figure 8:
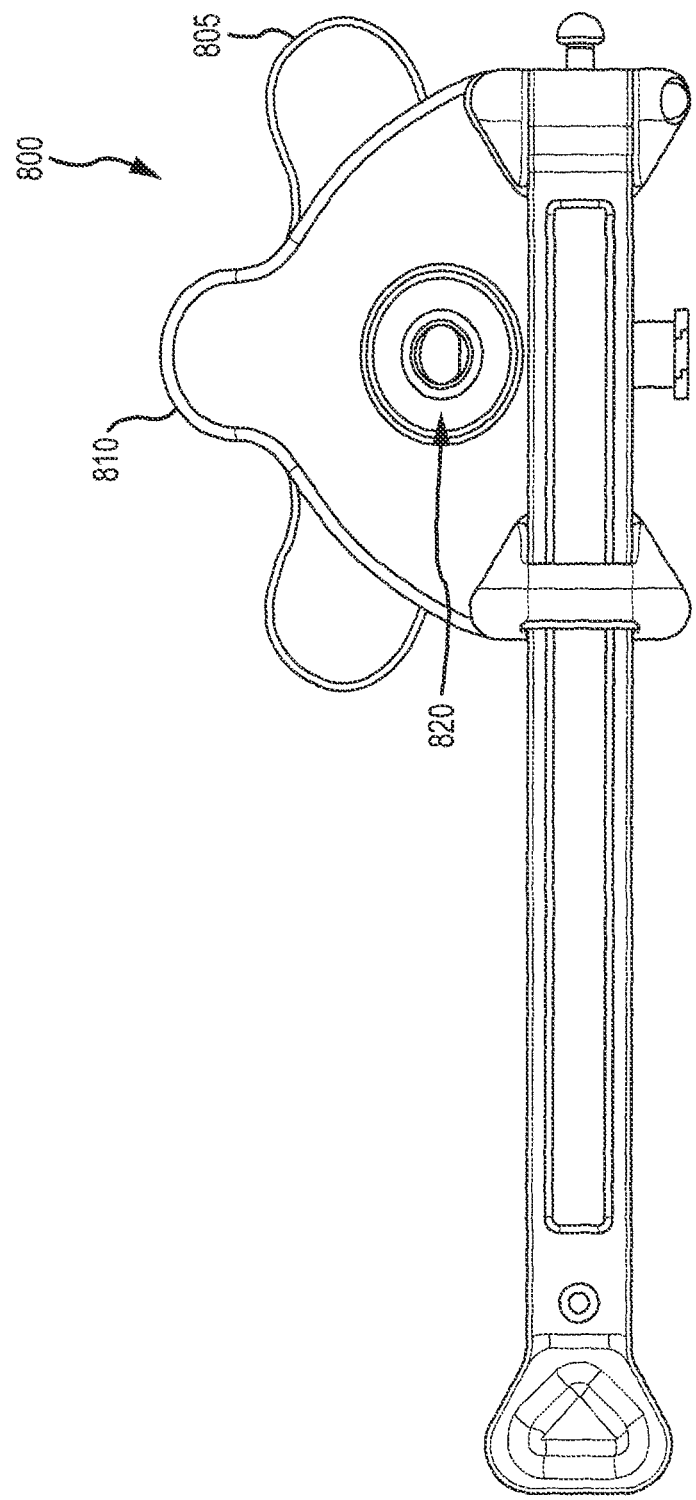
FIG. 8 shows aspects of scope and magnetic introducer systems and methods according to embodiments of the present invention.
Figure 9:
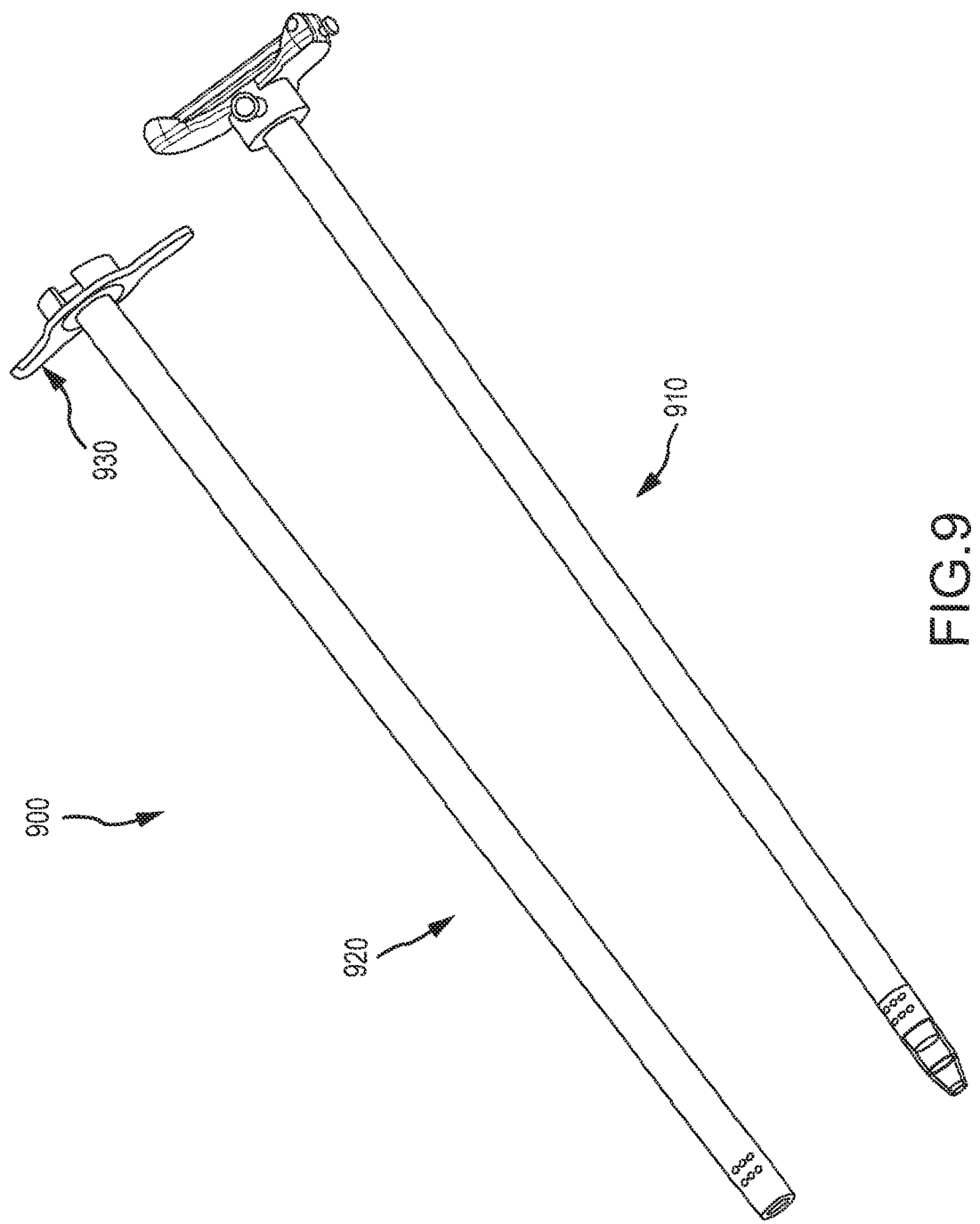
FIG. 9 illustrates aspects of scope and magnetic introducer systems and methods according to embodiments of the present invention.

In use, an exemplary treatment method may include inserting an endoscope (e.g. 5 mm) into an opening on the proximal end of the scope system a desired distance, for example until the endoscope can no longer advance. Advantageously, such a stop mechanism can be helpful to "seat" or locate the scope and ensure that the distal lens of the scope seats at the same location regardless of scope length used therefore providing a relatively consistent image for various length scopes. FIG. 8 depicts a treatment system 800 having a sheath 805 and a cannula or scope cap assembly 810. As shown here, scope cap assembly 810 includes a scope port 820 at a scope port location at a proximal end of a scope system 800. The surgeon or operator may pull the strap located on the proximal end of the device outward, and then over the light post of the endoscope and secure it over the designated button. The strap can include an elastomeric material, such that it can stretch to accommodate scopes of various lengths. As such, a custom scope may not be required and a variety of scopes may be accommodated. The operator may also connect the camera and light guide cable to the endoscope, and connect the female luer to standard wall suction or flush tubing. In some cases, methods may involve using a port, such as an 11 mm port, to introduce the system into the chest cavity, for example if insufflation is required or desired. if insufflation is not required or desired, an incision may be used instead of a port. The operator may introduce the system through the chest wall, and use the system to navigate/dissect tissue to reach the desired location in the thoracic space. If desired, the surgeon may detach the scope system from the sheath and withdraw it while holding the sheath in place during withdrawal. Optionally, the sheath can be used to deliver one or more desired surgical instruments or devices. In some cases, a scope system may be used in conjunction with an introducer system, an ablation device, or both. FIG. 9 depicts a treatment system 900 having a cannula or scope system 910 with a removable sheath 920 according to embodiments of the present invention. As shown here, removable sheath 920 includes a proximal section having an ergonomic flange 930.

Exemplary Embodiments (Section 4)

Figure 10:
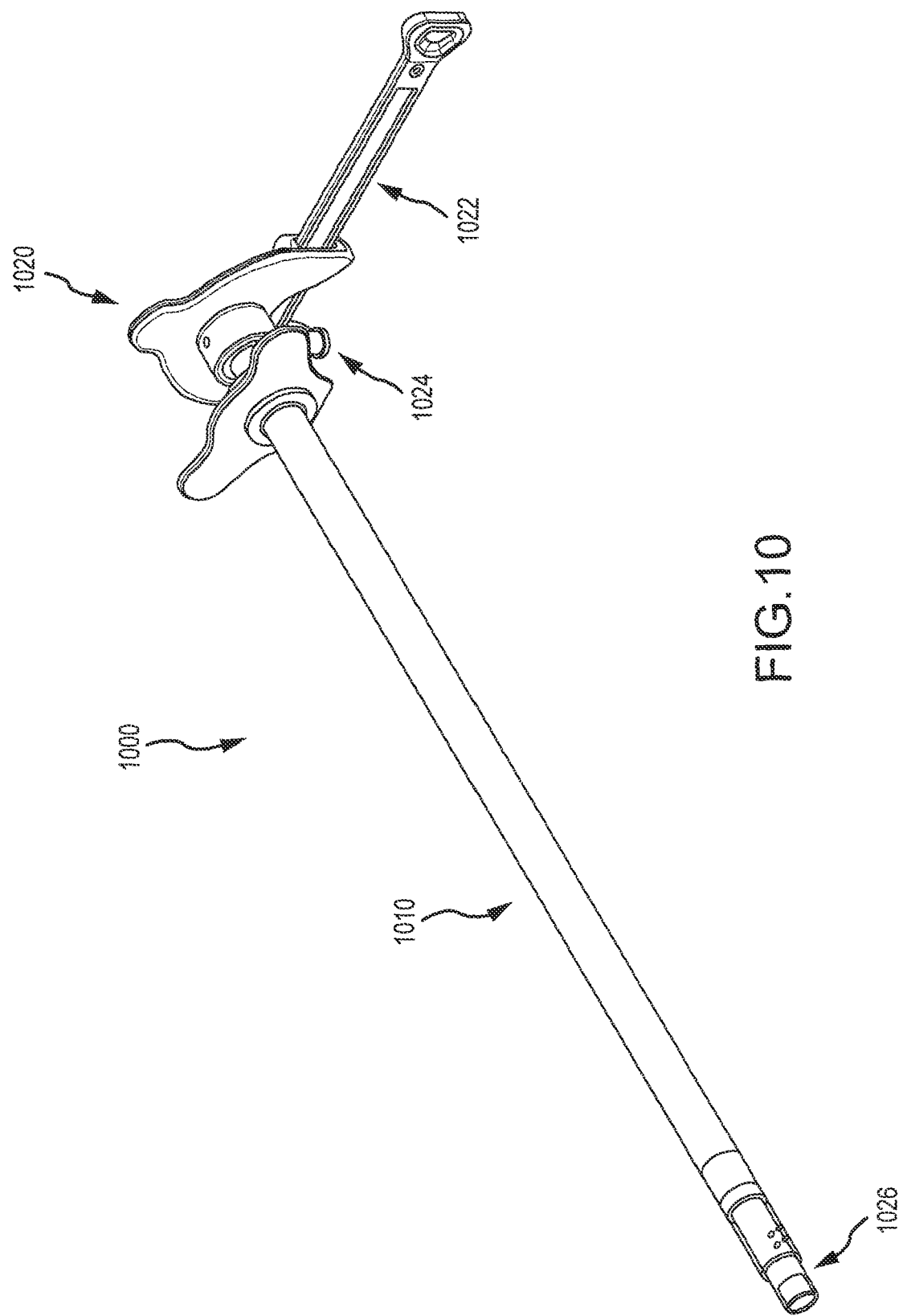
FIG. 10 depicts aspects of scope and magnetic introducer systems and methods according to embodiments of the present invention.
Figure 11:
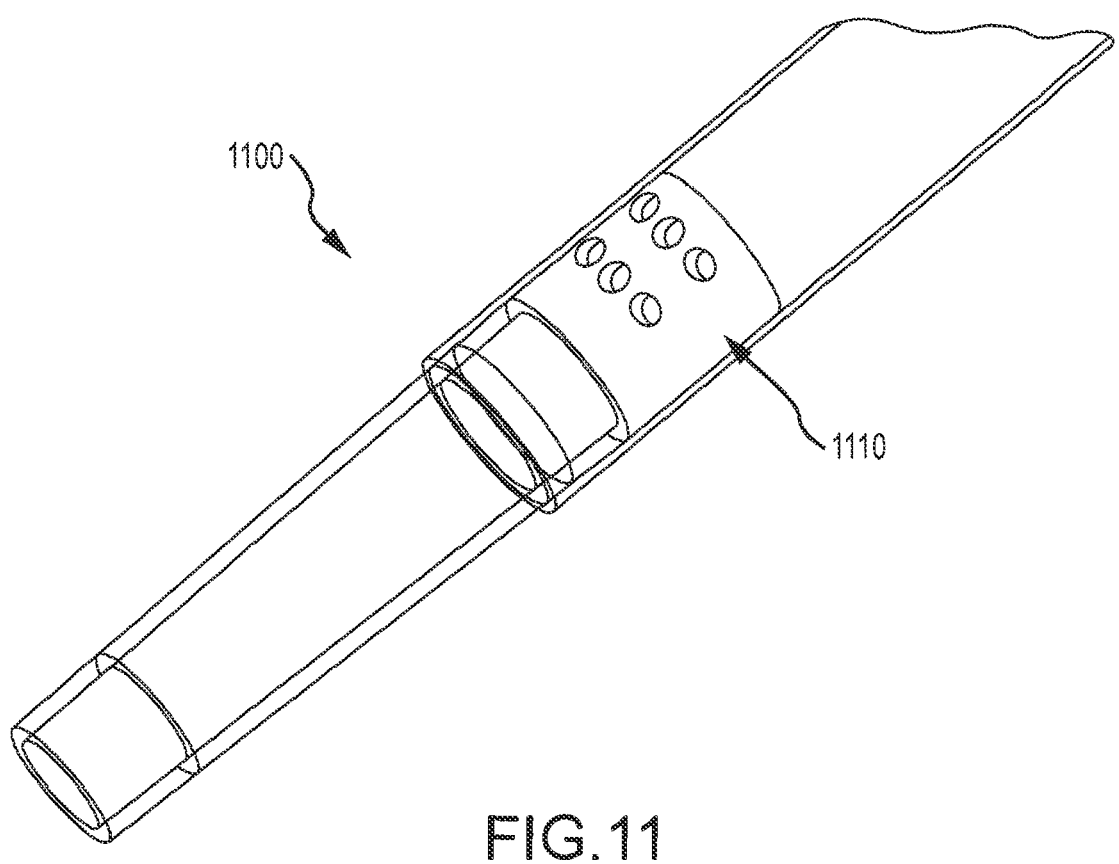
FIG. 11 illustrates aspects of scope and magnetic introducer systems and methods according to embodiments of the present invention.
Figure 15A:
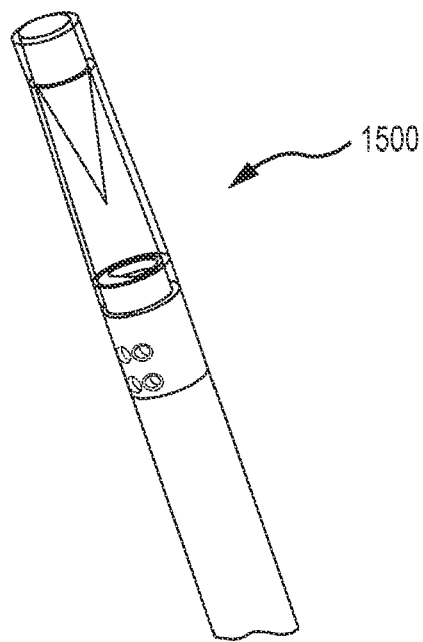
FIGS. 15A, 15B, 15C, and 15D show aspects of scope and magnetic introducer systems and methods according to embodiments of the present invention.
Figure 15B:
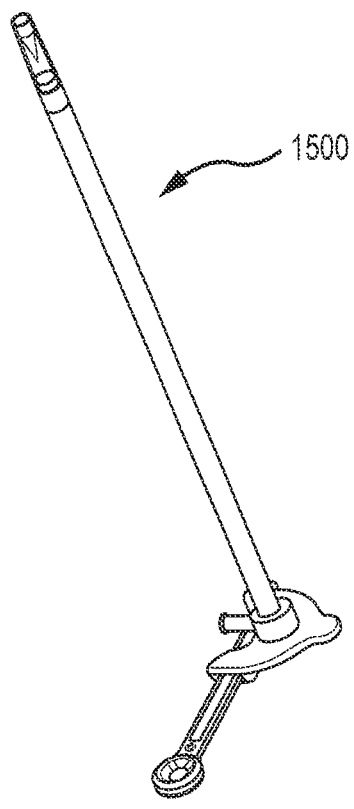
Figure 15C:
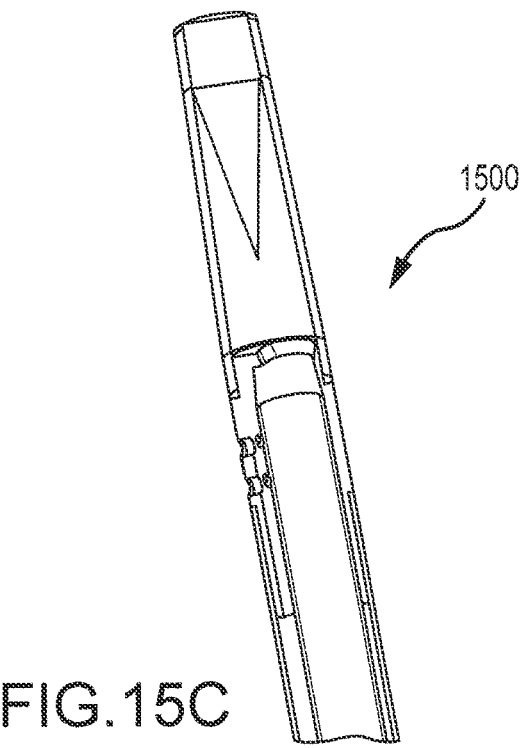
Figure 15D:
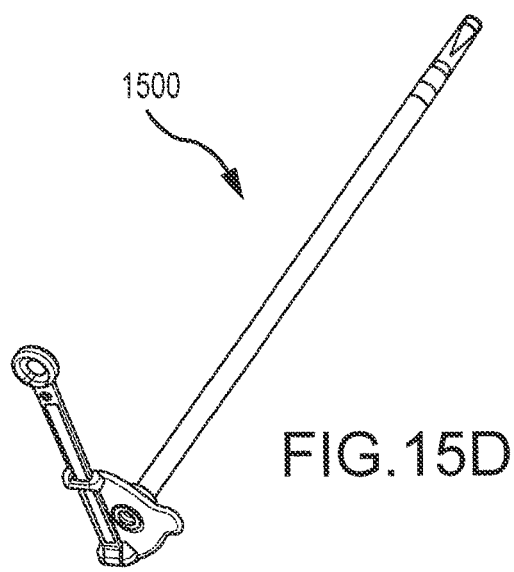
Figure 16A:
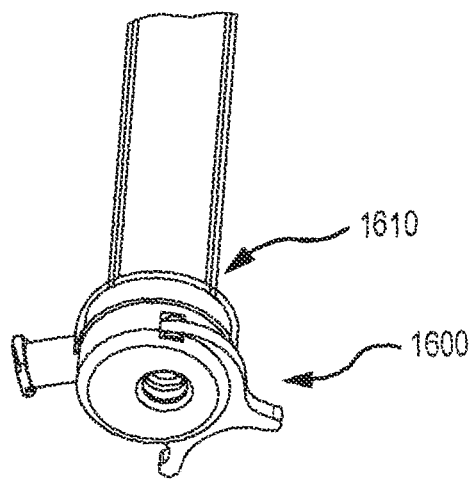
FIGS. 16A, 16B, 16C, 16D, and 16E illustrate aspects of scope and magnetic introducer systems and methods according to embodiments of the present invention.
Figure 16B:
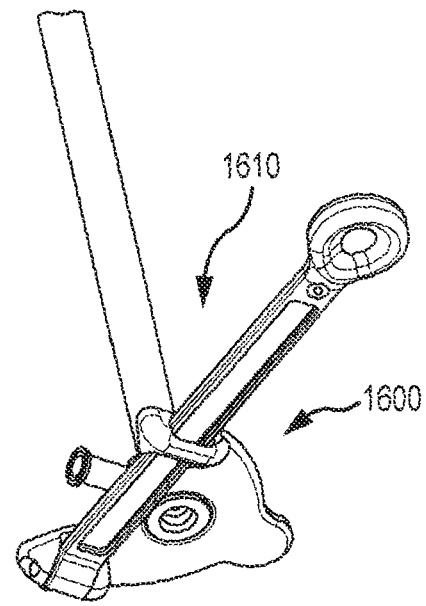
Figure 16C:
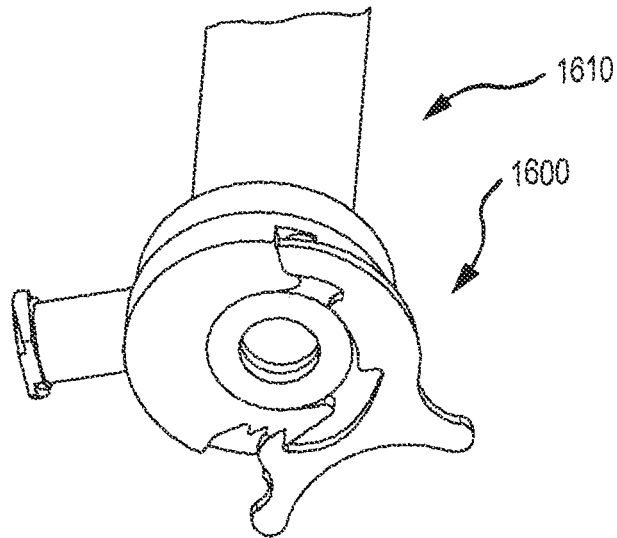
Figure 16D:
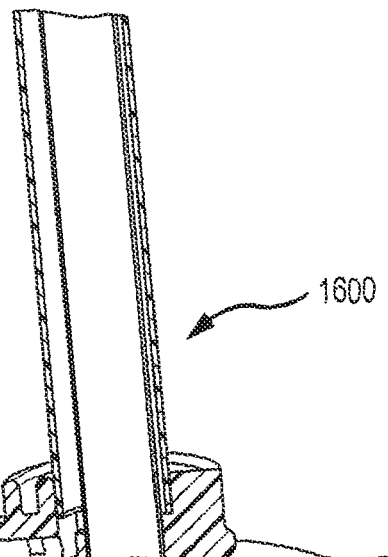
Figure 16E:
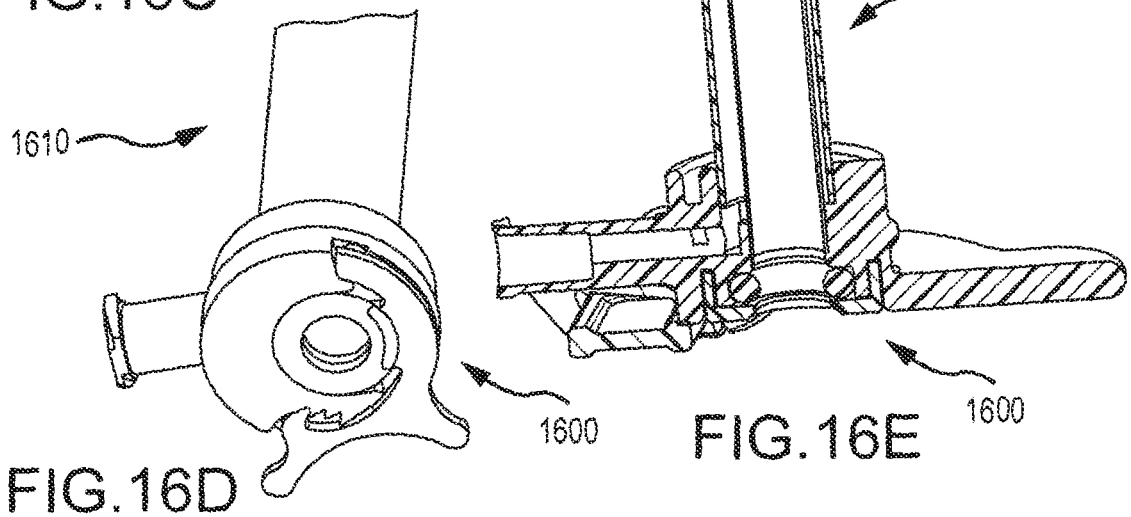
Figure 17A:
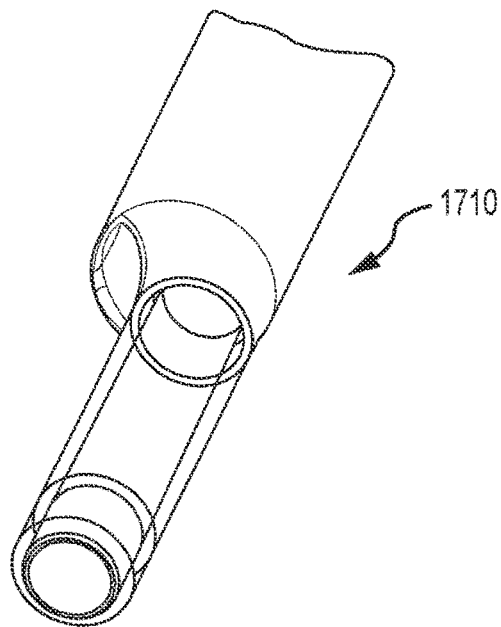
FIGS. 17A, 17B, 17C, and 17D show aspects of scope and magnetic introducer systems and methods according to embodiments of the present invention.
Figure 17B:
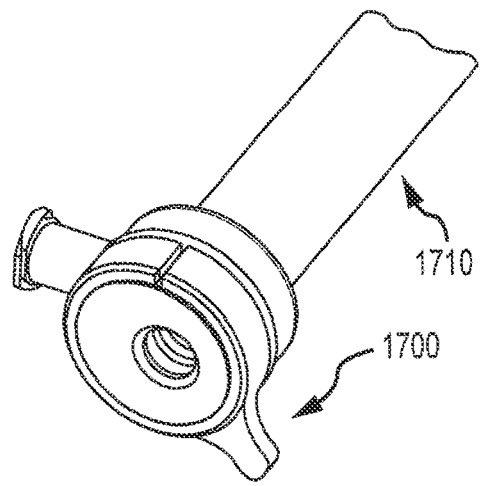
Figure 17C:
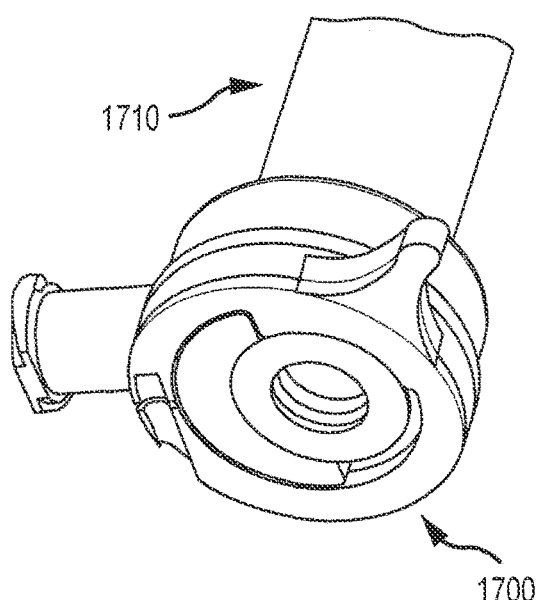
Figure 17D:
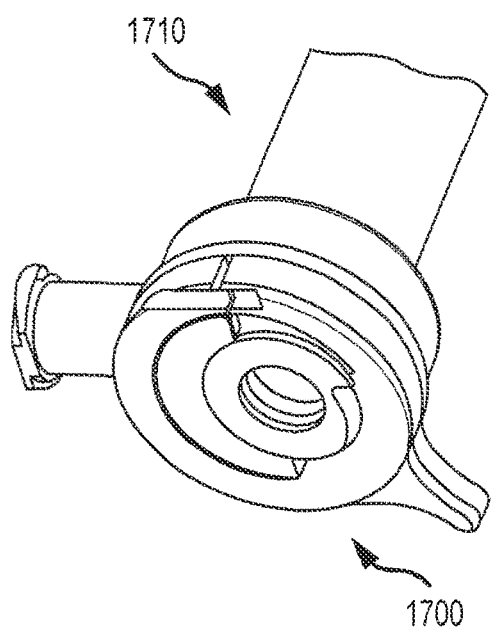

Magnetic introducer systems may be configured for use with ablation devices or as stand alone systems. An exemplary introducer system may include a scope system with a sheath, a magnetic introducer, and a stylet. In some cases, a magnetic introducer system or cannula can be configured to accommodate an endoscope (e.g. 5 mm). Introducer systems or cannulas may include features such as an optical window with magnet, a proximal housing with strap and luer for suction or flushing, an easy snap on/off flange and removable sheath. A service port on the proximal end of the system can have a female connector that can accommodate standard OR vacuum source or can be used for flushing purposes. FIG. 10 depicts features of an introducer system 1000 according to embodiments of the present invention. Introducer system 1000 includes a removable sheath 1010 and a scope system or cannula 1020. The removable sheath 1010 is configured to slidably received the scope system or cannula 1020. As shown here, scope system or cannula 1020 can include a scope strap 1022, a suction/flush port 1024, and a magnetic distal cap 1026. Introducer systems may include built-in suction/flush apertures at the distal end of the product. For example, as shown in FIG. 11, introducer system or cannula 1100 includes one or more suction/flush apertures 1110. Such apertures can be disposed at a distal section or end of a scope system.

As depicted in FIG. 12, an introducer system 1200 may include a magnetic introducer or cannula 1210 with an assembled sheath 1220, a magnetic introducer tubing 1230, and a stylet 1240. An introducer system may be indicated for minimally invasive surgery, and may provide access and visibility for delivery/placement of surgical instruments such as an ablation device. In some cases, an introducer system can be indicated for patients that may benefit from blunt dissection of tissue including structures in the thoracic space.

In use, an exemplary treatment method may include inserting an endoscope (e.g. 5 mm) into the opening on the proximal end of the a scope system or cannula, for example until the endoscope can no longer advance. FIG. 13 depicts a treatment system 1300 having a scope system or cannula 1305 configured for slidable placement within a sheath 1315. Scope system 1305 includes a scope port 1310 at a scope port location on a proximal location of a scope system or cannula 1305 according to embodiments of the present invention. The surgeon or operator may pull a strap 1320 located on the proximal end of the device or cannula 1305 outward, and then over the light post of the endoscope and secure it over the designated button. The operator may also connect the camera and light guide cable to the endoscope, and connect the female luer to standard wall suction or flush tubing. In some cases, methods may involve using a port, such as an 11 mm port, to introduce the system into the chest cavity, for example if insufflation is required or desired. If insufflation is not required or desired, an incision may be used instead of a port. The operator may introduce the system through the chest wall, and use the system to navigate/dissect tissue to reach the desired location in the thoracic space, for advancement of the magnetic introducer tubing. If desired, the surgeon may detach the magnetic scope system or cannula from the sheath and withdraw it while holding the sheath 1315 in place during withdrawal.

The operator may insert the distal end of the magnetic introducer tubing into the sheath 1315 and advance it until the second ring mark on the magnetic introducer tubing is aligned with the entrance of the sheath 1315. Utilizing a second port, the operator may introduce a scope system (with sheath detached) into the chest wall and navigate through the thoracic space to locate the distal-tip of the magnetic introducer tubing. When the magnetic scope system couples with the distal tip of the magnetic introducer tubing the operator can begin to slowly pull the magnetic scope system out of the port or created incision while advancing the magnetic introducer tubing into the other port.

If a magnetic introducer system is used in conjunction with a treatment device such as an ablation assembly, a distal portion of the treatment device or ablation assembly can be attached with a proximal section of the magnetic introducer tubing. In some cases, the operator may ensure that the stripe on both tubes is aligned. The operator may continue to pull the magnetic introducer tubing out of the port/incision, while advancing the treatment device or ablation assembly. When the distal portion or tubing of the ablation assembly is out of the chest wall, the operator can disconnect the magnetic introducer tubing from the device. In some cases, it may be desirable to use a stylet during the introduction of the magnetic introducer tubing in the luer of the sheath. FIG. 14 shows a treatment system 1400 such as a magnetic introducer system having a scope assembly or cannula 1410 with a removable sheath 1420 according to embodiments of the present invention. As shown here, scope assembly or cannula 1410 includes a magnetic distal cap 1412 and removable sheath 1420 includes an ergonomic flange 1422.

Exemplary Embodiments (Section 5)

FIGS. 15A, 15B, 15C, and 15D illustrate aspects of a cannula assembly or scope cap assembly 1500 according to embodiments of the present invention. In some cases, embodiments encompass a system for coupling a scope to a cannula assembly which protects its lens in wet or dry environments and additionally allows for fluid infusion, evacuation of fluids from the field, and instrument delivery and retrieval.

Exemplary coupling mechanisms may include an elastic strap which connects from one end of the proximal cannula assembly to the other around the scope, a light source cable, or a camera allowing for varying scope lengths and retaining scopes within the assembly under tension. O-rings sized to provide a frictional fit at the proximal end of the assembly to retrain the scope may be included as well.

FIGS. 16A, 16B, 16C, 16D, and 16E illustrate aspects of a coupling mechanism 1600 that can be used to connect a cannula assembly 1610 with a visualization or monitoring device such as a scope.

FIGS. 17A, 17B, 17C, and 17D illustrate aspects of a coupling mechanism 1700 that can be used to connect a cannula assembly 1710 with a visualization or monitoring device such as a scope.

According to some embodiments, as depicted in one or more of FIGS. 15A, 15B, 15C, 15D, 16A, 16B, 16C, 16D, 16E, 17A, 17B, 17C, and 17D, systems may include a cam-like locking assembly wherein a locking lever applies force to or compresses an o-ring or soft member against the scope shaft to increase pressure and friction. A luer fitting at the proximal end of the device may be capable of coupling with a syringe or tubing and can communicate through an internal lumen and terminate at the distal end of the device with a single or multiple port array to communicate saline irrigation or vacuum to clear the field of fluids near the visualization end of the device. A central lumen can be sealed to distal and proximal ports such that a second lumen allowing passage of the endoscope is sealed from communication with fluid.

In some instances, a magnet at the tip of the window can be capable of retrieving instruments and introducers. In alternate embodiments the magnet can be wired as an ablation electrode to visualize a region to be ablated, press the window against said tissue and ablate. An electrode embedded in the visualization window can take many forms/geometries such as a protruding spherical lead or ribbon type lead. Alternatively, the electrode can be a lead or strip integrated directly into the window such that the region being ablated can be more readily observed directly contacting the window. Such a window can be designed to have multiple leads/electrodes for ablating and also for pacing or sensing to assess electrical activity and the adequacy of lesions created in the treatment of arrhythmias. Spacing of multiple electrodes can provide for electrical isolation from one electrode to another. In other embodiments, these integrated ablation and pacing/sensing electrodes can be integrated into the sheath either directly over the window or just proximal or distal to the viewing window.

A cone may protrude from the tip of the visualization window to deflect light from the endoscope and minimize reflection and glare. Such features may be particularly useful with windows terminating in a large zone which is perpendicular to the light source. Various alternate geometries are also possible with the similar objective of minimizing the area of the tip of the viewing window that is perpendicular to the scope and its light source and deflecting or scattering the light. Such a mechanism can create an optical illusion in certain configurations such as a cone whereby the image viewed through the window is reflected back onto the cone resulting in the perception or appearance that the cone is transparent.

Systems may include a coaxial exchange sheath such that an assembly is passed into place, a cannula/visualization assembly is withdrawn leaving the sheath through which a guiding introducer can be passed into place. A sheath can be withdrawn over the introducer. A proximal end of the introducer can be coupled with an ablation or treatment device. The distal end can be retrieved with a magnetic visualization cannula. In some cases, a sheath can have a soft membrane at its tip to minimize potential abrasion.

As noted above, exemplary scope or introducer systems can be used with ablation assemblies and other treatment devices. Alternate systems can be equivalently designed on a smaller scale and can be used intravascularly or endocardially. Such embodiments can utilize flexible fiber optic or equivalent visualization technologies and miniature viewing windows with integrated ablating or pacing/sensing leads, flushing/suction ports, and magnetic tips as desired. Such configurations can allow a catheter to view the inside of the heart tissue as it abuts against it to ablate, pace, or sense electrical activity. A magnet of opposite polarity can guide such a device from outside the heart. When such a magnet is in contact with the epicardial tissue, it can be configured to also be an ablating and viewing element as described elsewhere herein. This approach can create a bipolar ablating element using an endocardial ablation catheter with integrated magnetic visualization and an epicardial ablation probe with integrated magnetic visualization tip. Such integrated visualization can be useful in more traditional epicardial ablation probes and clamps for small incision introduction.

Exemplary ablation systems can include an ablation energy source for providing energy to the ablation device. An ablation energy source is typically suited for use with ablation apparatus as described herein using RF energy. With regard to RF ablation, a typical RF ablation system includes a RF generator which feeds current to an ablation device, including those described in this application, containing a conductive electrode for contacting targeted tissue. The electrical circuit can be completed by a return path to the RF generator, provided through the patient and a large conductive plate, which is typically in contact with the patient's back. Embodiments encompass ablation using RF electrodes, including single RF ablation electrodes. Although ablation energy is often described herein in terms of RF energy, it is understood that embodiments are not limited to such ablation modalities, and other kinds of ablation energy sources and ablation devices may be used. Hence, with regard to the ablation techniques disclosed herein, other suitable ablation elements or mechanisms, instead or in addition to an RF electrode, can be used. Embodiments of the present invention therefore encompass any of a variety of ablation techniques, including without limitation infrared lasers, high intensity focused ultrasound (HIFU), microwave, Cryoablation (killing or damaging the tissue by freezing), chemical or biological agents, radiation, and the like. In some cases, an ablation mechanism can include an ablation element that transmits or delivers RF energy to patient tissue. Optionally, suitable ablation elements can transmit or deliver infrared laser energy, high intensity focused ultrasound (HIFU) energy, microwave energy, Cryoablation energy, chemical agents, biological agents, radiation energy, and the like. Embodiments encompass ablation mechanisms having multiple ablation elements, such as multiple RF electrodes. According to some embodiments, an ablation element may include a monopolar electrode. Relatedly, an ablation element may include a bipolar electrode. Any of these modalities is well suited for use in epicardial or endocardial ablation techniques resulting in electrical isolation and transmurality.

Exemplary Embodiments (Section 6)

In some cases, embodiments encompass systems and methods that involve the use of two introducers with ends carrying magnets of opposite polarities so that the ends join with an audible click as the ends approach one another. In some instances, no optical windows are used and the connection can be made with the surgeons blind to the connection region. As described elsewhere herein, a first introducer can placed into the oblique sinus and a second introducer can be placed into the transverse sinus, with both devices being introduced from the right side. The connection between the first and second introducers can be established near the left pulmonary veins. This approach has been observed to provide a simplified procedure for placing an ablation device its proper or desired location.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

We claim:

1. A magnetic introducer device for use with an imaging device and for placing a treatment device at a location within a patient, the magnetic introducer device comprising:
   a cannula assembly having a first lumen and a second lumen, wherein the first lumen extends into a distal portion of the cannula assembly, the first lumen is configured to receive the imaging device and where the second lumen includes an aperture near a distal section of the cannula assembly;
   a connection port at a proximal end of the cannula assembly configured to provide fluid communication for flushing or suction through the aperture; and where the proximal end of the cannula assembly is configured to removably attach to the treatment device;

a magnetic scope cap at a distal end of the cannula assembly and having a magnet at a distal tip and an optical window proximal to the magnet extending circumferentially and entirely around the magnetic scope cap, wherein the optical window facilitates visualization of tissue within the patient when the imaging device is inserted within the first lumen;

a sheath assembly configured to permit slidable placement and removal of the cannula assembly; and a magnetic introducer tubing assembly configured for slidable placement within the sheath assembly once the cannula assembly has been removed, the magnetic introducer tubing assembly comprising a tip that is retrievable via the magnet of the magnetic scope cap.

2. The magnetic introducer device of claim 1, further comprising a strap at the proximal end of the cannula assembly to removably attach to the treatment device.

3. The magnetic introducer device of claim 1, wherein the distal end of the cannula assembly carries a pacing electrode.

4. The magnetic introducer device of claim 1, wherein the distal end of the cannula assembly carries an ablation element.

5. The magnetic introducer device of claim 4, wherein the ablation element apply an energy selected from a radiofrequency energy, a microwave energy, an ultrasonic energy, a cryogenic energy.

6. The magnetic introducer device of claim 1, wherein the magnetic introducer tubing assembly comprises a preformed bend.

7. The magnetic introducer device of claim 1, wherein the optical window of the magnetic scope cap is sealed to prevent liquid and tissue from contacting the imaging device.

8. The magnetic introducer device of claim 1, wherein the optical window of the magnetic scope cap is not sealed to prevent liquid and tissue from contacting the imaging device.

* * * * *